(12) United States Patent
Chan et al.

(10) Patent No.: US 7,674,955 B2
(45) Date of Patent: Mar. 9, 2010

(54) **TRANSCRIPTION FACTOR GENE INDUCED BY WATER DEFICIT CONDITIONS AND ABSCISIC ACID FROM *HELIANTHUS ANNUUS*, PROMOTER AND TRANSGENIC PLANTS**

(75) Inventors: Lia Raquel Chan, Provincia de Santa Fe (AR); Daniel Hector Gonzalez, Provincia de Santa Fe (AR); Carlos Alberto Dezar, Provincia de Santa Fe (AR); Gabriela Marisa Gago, Provincia de Santa Fe (AR)

(73) Assignee: Bioceres, S.A., Rosario, Santa Fe (AR)

( * ) Notice: Subject to any disclaimer, the term of this patent is extended or adjusted under 35 U.S.C. 154(b) by 1317 days.

(21) Appl. No.: 10/520,033

(22) PCT Filed: May 2, 2003

(86) PCT No.: PCT/US03/13770

§ 371 (c)(1),
(2), (4) Date: Dec. 30, 2004

(87) PCT Pub. No.: WO2004/099365

PCT Pub. Date: Nov. 18, 2004

(65) Prior Publication Data

US 2007/0180584 A1 Aug. 2, 2007

(51) Int. Cl.
C12N 15/82 (2006.01)
C12N 5/04 (2006.01)
A01H 5/00 (2006.01)
A01H 5/10 (2006.01)

(52) U.S. Cl. .................... 800/298; 800/320; 800/278; 435/419

(58) Field of Classification Search ............... None
See application file for complete search history.

(56) References Cited

U.S. PATENT DOCUMENTS 5,981,729 A 11/1999 Chun et al.
6,265,638 B1 * 7/2001 Bidney et al. .............. 800/294

FOREIGN PATENT DOCUMENTS

WO WO 01/77311 A2 10/2001

OTHER PUBLICATIONS

Chan et al. (NCBI, GenBank Sequence Accession No. AF339748, Published Mar. 26, 2001).*
Gago et al. (NCBI, GenBank Sequence Accession No. AF339749, Published Mar. 26, 2001).*
Chan et al. (NCBI, GenBank Sequence Accession No. AF329463, Published Mar. 2, 2001).*
Gago et al. (NCBI, GenBank Sequence Accession No. AF339749, Published Mar. 2001).*
Wells (Biochemistry 29:8509-8517, 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Heim et al. (Mol. Biol. Evol., 20(5):735-747, 2003).*
Gago et al. (Plant, Cell and Environment, 25:633-640, Published May 1, 2002).*
Bray, E.A., "Molecular Responses to Water Deficit," *Plant Physiol.* 103:1035-1040, American Society of Plant Physiologists (1993).
Carabelli, M., et al., "The *Arabidopsis Athb-2* and -4 genes are strongly induced by far-red-rich light," *Plant J.* 4:469-479, Blackwell Scientific Publishers (1993).
Century, K., et al., "Regulating the Regulators: The Future Prospects for Transcription-Factor-Based Agricultural Biotechnology Products," *Plant Physiol.* 147:20-29, American Society of Plant Physiologists (May 2008).
Chan, R.L., et al., "Homeoboxes in plant development," *Biochim. Biophys. Acta.* 1442:1-19, Elsevier Publishing Company (1998).
Gago, G.M., et al.,"*Hahb-4*, a homeobox-leucine zipper gene potentially involved in abscisic acid-dependent responses to water stress in sunflower," *Plant Cell Environ.* 25:633-640, Blackwell Scientific Publications (May 2002).
Gehring, W.J., "Homeo boxes in the study of development," *Science* 236:1245-1252, American Association for the Advancement of Science (1987).
Gehring, W.J., et al., "Homeodomain Proteins," *Annu. Rev. Biochem.* 63:487-526, Annual Reviews (1994).
Hjellström, M., et al., "Constitutive expression of the water deficit-inducible homeobox gene *ATHB7* in transgenic *Arabidopsis* causes a suppression of stem elongation growth," *Plant Cell Environ.* 26:1127-1136, Blackwell Scientific Publications (Jun. 2003).
Ingram, J., and Bartels, D., "The Molecular Basis Of Dehydration Tolerance In Plants," *Annu. Rev. Plant Physiol. Plant Mol. Biol.* 47:377-403, Annual Reviews Inc. (1996).
Lee, Y-H., and Chun, J-Y., "A new homeodomain-leucine zipper gene from *Arabidopsis thaliana* induced by water stress and abscisic acid treatment," *Plant Mol. Biol.* 37:377-384, Kluwer Academic (1998).
Leung, J., and Giraudat, J., "Abscisic Acid Signal Transduction," *Annu. Rev. Plant Physiol. Plant Mol. Biol.* 49:199-222, Annual Reviews Inc. (1998).
Liu, Q., et al., "Two Transcription Factors, *DREB1* and *DREB2*, with an EREBP/AP2 DNA Binding Domain Separate Two Cellular Signal Transduction Pathways in Drought- and Low-Temperature-Responsive Gene Expression, Respectively, in *Arabidopsis*," *Plant Cell* 10:1391-1406, American Society of Plant Physiologists (1998).

(Continued)

*Primary Examiner*—Stuart F. Baum
(74) *Attorney, Agent, or Firm*—Sterne, Kessler, Goldstein & Fox P.L.L.C.

(57) ABSTRACT

A new transcription factor coding gene induced by water deficit or abscisic acid of *Helianthus annuus*, having a homeodomain associated to a leucine zipper, was characterized. The transcription factor is useful to be cloned in DNA constructions for transforming host cells and plants. The transgenic plants comprising the transcription factor gene are tolerant and resistant to harmful environmental conditions such as water stress and high salinity. A nucleic acid promoting sequence is also provided wherein the sequence is induced by water deficit or abscisic acid. Constructions, host cells and transgenic plants that comprise the transcription factor gene are provided.

14 Claims, 13 Drawing Sheets

OTHER PUBLICATIONS

Nakashima, K., and Yamaguchi-Shinozaki, K., "Molecular Studies on Stress-Responsive Gene Expression in *Arabidopsis* and Improvement of Stress Tolerance in Crop Plants by Regulon Biotechnology," *JARQ* 39:221-229, Japan International Research Center for Agricultural Sciences (Oct. 2005).

Olsson, A.S., et al., "The homeobox genes *ATHB12* and *ATHB7* encode potential regulators of growth in response to water deficit in *Arabidopsis*," *Plant Mol. Biol.* 55:663-677, Kluwer Academic (Jul. 2004).

Palena, C.M., "A monomer-dimer equilibrium modulates the interaction of the sunflower homeodomain leucine-zipper protein Hahb-4 with DNA," *Biochem. J.* 341:81-87, Portland Press (1999).

Pimentel, D., et al., "Water Resources: Agriculture, the Environment and Society," *BioScience* 47:97-106, American Institute of Biological Sciences (1997).

Schena, M., et al., "The *HAT4* gene of *Arabidopsis* encodes a developmental regulator," *Genes Dev.* 7:367-379, Cold Spring Harbor Laboratory Press (1993).

Sessa, G., et al., "The Athb-1 and -2 HD-Zip domains homodimerize forming complexes of different DNA binding specificities," *EMBO J.* 12:3507-3517, Oxford University Press (1993).

Sessa, G., et al., "DNA-binding Specificity of the Homeodomain-leucine Zipper Domain," *J. Mol. Biol.* 274:303-309, Academic Press (1997).

Shinozaki, K., and Yamaguchi-Shinozaki, K., "Gene Expression and Signal Transduction in Water-Stress Response," *Plant Physiol.* 115:327-334, American Society of Plant Physiologists (1997).

Söderman, E., et al., "The *Arabidopsis* homeobox gene *ATHB-7* is induced by water deficit and by abscisic acid," *Plant J.* 10:375-381, Blackwell Scientific Publishers (1996).

Söderman, E., et al., "The HD-Zip gene *ATHB6* in *Arabidopsis* is expressed in developing leaves, roots and carpels and up-regulated by water deficit conditions," *Plant Mol. Biol.* 40:1073-1083, Kluwer Academic (1999).

Bray, E.A., "Plant Responses to Water Deficit," *Trends Plant Sci.* 2:48-54, Elsevier Science, Ltd. (1997).

Examiner's First Report on corresponding Australian Patent Application No. 2003237161, mailed Jun. 23, 2009, 3 pgs.

Brandle, J.E. et al., "Leaf ESTs from Stevia rebaudiana: A resource for gene discovery in diterpene synthesis", Plant Physiol. 2001, (GenBank Accession No. BG522661, entered Nov. 16, 2001), 2 pgs.

* cited by examiner

```
+1    TCACTAGTACCATAATATTCACAAACACACACACCTCAGAAACGAAGCTTGC
+53   ACATAATGTCTCTTCAACAAGTACCCACAACAGAAACAACCACCAGGAAGAA
1          M  S  L  Q  Q  V  P  T  T  E  T  T  T  R  K  N
+105  CCGAAACGAGGGGCGGAAACGATTTACCGACAAACAAATAAGTTTCCTAGAG
17     R  N  E  G  R  K  R  F  T  D  K  Q  I  S  F  L  E
+157  TACATGTTTGAGACACAGTCGAGACCCGAGTTAAGGATGAAACACCAGTTGG
34     Y  M  F  E  T  Q  S  R  P  E  L  R  M  K  H  Q  L
+209  CACATAAACTCGGGCTTCATCCTCGTCAAGTGGCGATATGGTTCCAGAACAA
51     A  H  K  L  G  L  H  P  R  Q  V  A  I  W  F  Q  N  K
+261  ACGCGCGCGATCAAAGTCGAGGCAGATTGAGCAAGAGTATAACGCGCTAAAG
69      R  A  R  S  K  S  R  Q  I  E  Q  E  Y  N  A  L  K
+313  CATAACTACGAGACGCTTGCGTCTAAATCCGAGTCTCTAAAGAAAGAGAATC
86      H  N  Y  E  T  L  A  S  K  S  E  S  L  K  K  E  N
+365  AGGCCCTACTCAATCAGgtatggttgcaaacttacaatgttgcattcaacta
103     Q  A  L  L  N  Q
+417  tttaagtagttttgaattttgtgacaataaagattgacaaatgttgtttga
+469  taattgattaacagTTGGAGGTGCTGAGAAATGTAGCAGAAAAGCATCAAGA
109              L  E  V  L  R  N  V  A  E  K  H  Q  E
+521  GAAAACTAGTAGTAGTGGCAGCGGTGAAGAATCGGATGATCGGTTTACGAAC
122    K  T  S  S  S  G  S  G  E  E  S  D  D  R  F  T  N
+573  TCTCCGGACGTTATGTTTGGTCAAGAAATGAATGTTCCGTTTTGCGACGGTT
139    S  P  D  V  M  F  G  Q  E  M  N  V  P  F  C  D  G
+625  TTGCGTACTTTGAAGAAGGAAACAGTTTGTTGGAGATTGAAGAACAACTGCC
156    F  A  Y  F  E  E  G  N  S  L  L  E  I  E  E  Q  L  P
+677  AGACCCTCAAAAGTGGTGGGAGTTCTAAAGAGTAAAGAAGGATGTAGAAGTA
174       D  P  Q  K  W  W  E  F  *
+729  GTAGAGTAAAAACTAAAACATACCAGATAGTTGGTTTACACTTTGT
```

Athb-1   LPEKKRRLTTEQVHLLEKSFETENKLEPERKTQLAKKLGLQPRQVAVWFQNRRARWKTKQLERDYDLLKSTYDQLLSNYDSIVMDNDKLRSEVTSLTEK
Athb-6   LSEKKRRLSINQVKALEKNFELENKLEPERKVKLAQELGLQPRQVAVWFQNRRARWKTKQLEKDYGVLKTQYDSLRHNFDSLRRDNESLLQEISKLKTE
Athb-7   NKNNQRRFSDEQIKSLEMMFESETRLEPRKKVQLARELGLQPRQVAIWFQNKRARWKSKQLETEYNILRQNYDNLASQFESLKKEKQALVSELQRLKEA
Athb-12  KSNNQKRFNEEQIKSLELIFESETRLEPRKKVQVARELGLQPRQMTIWFQNKRARWKTKQLEKEYNTLRANYNNLASQFEIMKKEKQSLVSELQRLNEE
Hahb-4   RNEGRKRFTDKQISFLEYMFETQSRPELRMKHQLAHKLGLHPRQVAIWFQNKRARSKSRQIEQEYNALKHNYETLASKSESLKKENQALLNQLEVLRNV

FIG. 1

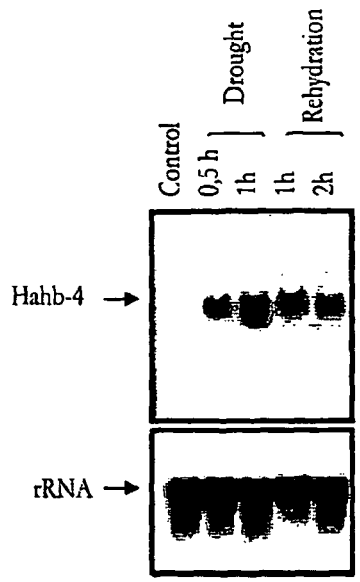
FIG. 3
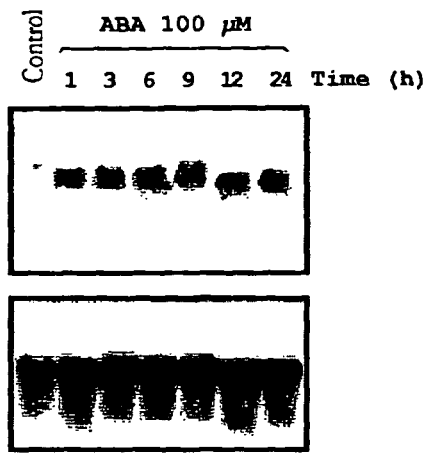
FIG. 4
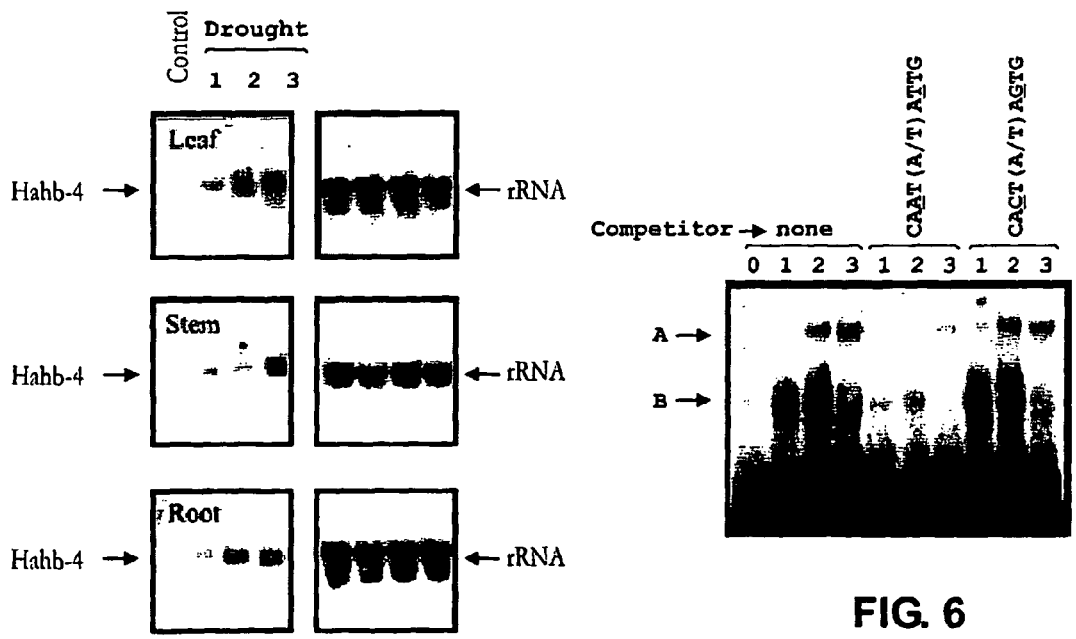
FIG. 5
FIG. 6

```
-1221 GATCCAATTGGACCACCTGGCACATCGTATCTTATCTCTTTTGTCGTTTCCAACA
-1166 CACCACAACACACCTACAAACGTGTCAATTCACACTTCACCAATTTCATTTCCTT
-1111 TTAGTCAATCATATTAAAAGTAGTAGCCCCCACCCCCATTTGTTACCTACCATTT
-1056 CCCACTTTAATAATCACCCACGCTATGTCCACTTGTACTTTTGTTTGCACACAAC
-1001 TCTTACCCATAAAATATCAAACCAAATTTTTTTAGTGGAAAACAAATTCCCCAA
 -946 ATAGAATACTAACGAAATTCATCGCATCAGAATACACTCATCTCTGAACAGTGGC
 -891 GAAGCTTGACGTTTTCGACGGGGGGTCGGAAAACGTATGTACCCGAAATTTCTAT
 -836 AGAATCGGGGGGTCGAAAACGTATATACCCAAAATTTCTATACGAAAACTACATA
 -781 TATAACACTACTGAGCAAAAAGTTCGGGGGTTCGGGCGCCCTCCCGGCCCCTTCA
 -726 AAGCTTCGCCAATGTCTCTGAACCGAAGAAAACCCTCACTCGTCTACTAGCCAAT
 -671 GAATCCTCACCAGGGAAAACCCTCACTCGTCTTACTGGACTATTGGCGCTTCCAA
 -616 ATGGACTACTTGCGAAATTCACCACATCGGGATACACTCGTCTACTGCGGTGAGG
 -561 TAAAACCCGCTTGGCTCAAGGGTACGAACTAGCGATTGCTGCCTACTCGCCTAAT
 -506 CTCCATCATCAACAGGTGCCGCCGAACAAATGCTGGGGCGGAGTTGAAGCCTAGG
 -451 GTCCAGTGACGCACCCATGAATTTTTTTCTAGGGATGCGAACGAGTGGTTTAACC
 -396 ATACTTTTAAGAGGTGCGGATCGGAAATTTTACCTATAAAATACACTAAAAAAGT
 -341 TCCAAGGGTCCACCCACCCCTTAACCTAAGTCCGCCTTTGTCTGGATCACGTGAA
 -286 ACATCAGGTCTCTCCCTTACCAGTCCAGCTACGACTCATTGACAAAATATCAAAA
 -231 CCATATGATTTTGAGTTTTATCTCAACCGAAAGTGACATCATGACAGAGAATCGA
 -176 CATAACCAAAACGTGTAAACGTACAACTCACCATTGCGTTGAAAAGGACAGAACA
 -121 GGTAGGATTCTCGTCAAATTCAACGCGTACACCTGTGCTTCATCTAAACCCCATA
  -66 CTTTTAAGAACCTTTATAAAGACCACTCACTATATATACACATATATAATATCAC
  -11 TTATCAAACCC+1
```

FIG. 18

TRANSCRIPTION FACTOR GENE INDUCED BY WATER DEFICIT CONDITIONS AND ABSCISIC ACID FROM *HELIANTHUS ANNUUS*, PROMOTER AND TRANSGENIC PLANTS

REFERENCE TO A SEQUENCE LISTING SUBMITTED ELECTRONICALLY VIA EFS-WEB

The content of the electronically submitted sequence listing (Name: substitute_sequence_listing.txt, Size: 16.5 kilobytes; and Date of Creation: May 20, 2009) is herein incorporated by reference in its entirety.

BACKGROUND OF THE INVENTION

1. Field of the Invention

The present invention relates to a new gene that encodes a transcription factor induced by water deficit conditions and abscisic acid from *Helianthus annuus*, having a homeodomain associated to a leucine zipper. The transcription factor is useful to be cloned in DNA constructions for transforming host cells and plants. The transgenic plants comprising the transcription factor are resistant to harmful environment conditions such as the water deficit stress and high salinity. A nucleic acid promoting sequence is also provided wherein the sequence is inducible by water deficit or abscisic acid, constructions, host cells and transgenic plants that comprise the sequence.

2. Description of the Prior Art

The homeodomain is a 60 amino acid motif present in a number of eukaryotic transcription factors involved in developmental processes (Gehring, Science 236, 1245-1252, 1987). Genes containing homeoboxes have been isolated from many eukaryotic organisms including fungi, mammals and plants (Gehring, W. J., et al., Annu. Rev. Biochem. 63, 487-526, 1994). Plant homeoboxes can be divided into several families according to sequence conservation and structure in and outside the homeodomain (Chan, R. L., et al. Biochim. Biophys. Acta 1442 (1), 1-19, 1998). Members of one of these families have a distinct feature: they code for proteins termed Hd-Zip, because they contain an homeodomain associated with a leucine zipper, a coiled-coil structure involved in dimerization. Hd-Zip proteins bind DNA efficiently only as dimers (Sessa, G., et al., EMBO J. 12, 3507-3517, 1993; Palena C. M., et al., Biochem J. 341, 81-87, 1999). It has been suggested that these proteins may be involved in regulating developmental processes associated with the response of plants to environmental conditions (Chan, R. L., et al. Biochim. Biophys. Acta 1442 (1), 1-19, 1998, Carabelli, M., et al., Plant J. 4, 469-479, 1993; Schena, M., et al., Genes Devel. 7, 367-379, 1993). One of the most common environmental stresses to which plants are exposed is dehydration. Although many seeds tolerate extreme dehydration, tolerance is rare in vegetative parts of the plant. Plants respond to water stress with the expression of a specific set of genes, which allows them to adapt to the altered environmental conditions (Bray, E. A. Trends Plant Sci. 2, 48-54, 1997 y Shinozaki, K. and Yamaguchi-Shinozaki, K. Plant Physiol. 115, 327-334, 1997). The hormone abscisic acid (ABA) plays an important role in a sub-set of these responses (Shinozaki, K. and Yamaguchi-Shinozaki, K. Plant Physiol. 115, 327-334, 1997 y Leung, J. and Giraudat, J. Ann. Rev. Plant Physiol. Plant Mol. Biol. 49, 199-222, 1998).

The characterization of the promoting regions of the genes involved in the tolerance or resistance to water stress shown the existence of an element that responds to ABA, namely ABRE, and an element responding to desiccation, namely DRE.

Söderman et al. have disclosed [described] the [two] genes, ATHB-7 and -6 of *Arabidopsis* that is [are] induced by abscisic acid and water deficit (Söderman E. et al., The Plant Journal 10: 375-381, 1996 and Soderman E. et al. Plant Molecular Biology 40: 1073-1083, 1999). The authors have not shown that the over-expression of these genes provide tolerance to water deficit.

U.S. Pat. No. 5,981,729 discloses a new gene that is induced by water deficit and abscisic acid and that encodes a transcription factor of *A. Thaliana*. This patent does not discloses any reference to transgenic plants carrying the gene of the present invention and resisting to water stress conditions.

SUMMARY OF THE INVENTION

It is therefore an object of the invention to provide an isolated nucleic acid molecule encoding the transcription factor Hahb-4, a functionally active fragment or variant thereof, having the nucleic acid sequence of SEQ ID NO:1 or a fragment thereof, wherein the nucleic acid molecule is derived from *Helianthus annuus*, and it may be an mRNA or the cDNA of SEQ ID NO:2, wherein the molecule is capable of binding to a 5'-CAAT(A/T)ATTG-3' DNA sequence (SEQ ID NO:23) or to a dehydration transcription regulating region of plant species.

It is still another object of the present invention to provide a vector, comprising a promoter operably linked to the nucleic acid sequence selected from the group comprising of SEQ ID No 1, SEQ ID No 2 and fragments thereof, wherein the vector drives the expression of the transcription factor Hahb-4 or a functionally active fragment or variant thereof, and wherein said transcription factor Hahb-4 or a functionally active fragment or variant thereof is capable of binding to a dehydration transcription regulating region of plant species, and wherein the expression of the vector in a host cell increases the tolerance of the cell to environmental stress, such as water stress, as compared to a wild type variety of such host cell.

It is a further object of the present invention to provide a transgenic plant stably transformed with a nucleic acid molecule having a sequence selected from the group comprising SEQ ID No 1, SEQ ID No 2 or fragments thereof, wherein the nucleic acid molecule encodes the transcription factor Hahb-4 or a functionally active fragment or variant thereof, and wherein the plant is provided with an increased tolerance to environmental stress, such as drought, salinity, osmotic, and others, preferably water stress, as compared to a wild type variety of such plant, and wherein the plant that may be a monocot, a dicot or any other agronomic one, is water stress tolerant by binding the transcription factor Hahb-4 or a functionally active fragment or variant thereof to a dehydration transcription regulating region of plant.

It is a further object of the present invention to provide a plant seed stably transformed with a nucleic acid molecule having a sequence selected from the group comprising SEQ ID No 1, SEQ ID No 2 and fragments thereof, wherein the nucleic acid molecule sequence encodes the transcription factor Hahb-4 or a functionally active fragment or variant thereof.

It is a further object of the present invention to provide a host cell that has been stably transformed with a nucleic acid molecule having a sequence selected from the group comprising SEQ ID No 1, SEQ ID No 2 and fragments thereof, wherein the nucleic acid molecule encoding the transcription factor Hahb-4 or a functionally active fragment or variant thereof, wherein the host cell is selected from the group comprising bacterial, fungal, insect, plant and animal cell and preferably it is a plant cell.

It is a further object of the present invention to provide a method of producing a water stress tolerant transgenic plant, the method comprising stably transforming a plant cell or cell culture with the nucleic acid sequence selected from the group comprising SEQ ID No 1, SEQ ID No 2 and fragments thereof, and regenerating the cells or cell cultures into plants.

It is another object of the present invention to provide an isolated nucleic acid molecule selected from the group comprising:

(a) a nucleic acid molecule having the nucleotide sequence SEQ ID No 3;
(b) a nucleic acid molecule having the nucleotide sequence SEQ ID No 10;
(c) a nucleic acid molecule having the nucleotide sequence of nucleotides 805 to 1221 of SEQ ID No 3;
(d) a nucleic acid molecule having the nucleotide sequence of nucleotides 904 to 1221 of SEQ ID No 3;
(e) a nucleic acid molecule having the nucleotide sequence of nucleotides 1011 to 1221 of SEQ ID No 3;
(f) a nucleic acid molecule having the nucleotide sequence of nucleotides 15 to 622 of SEQ ID No 3;
(g) a nucleic acid molecule having the nucleotide sequence of nucleotides 15 to 409 of SEQ ID No 10;
(h) a nucleic acid molecule having a nucleotide sequence complementary to the nucleic acid molecule of (a), (b), (c), (d), (e), (f) or (g); and
(i) a nucleic acid molecule having a length of at least 150 nucleotides and having at least 80% sequence identity to the nucleic acid molecule of (a), (b), (c), (d), (e), (f), (g) or (h), wherein said nucleic acid molecules are capable of promoting expression of a heterologous nucleic acid molecule in a transformed cell or tissue selected from the group comprising bacteria, fungal, insect, plant [or] animal cell, embryogenic tissue, plant callus and plant seed.

It is a further object of the present invention to provide a nucleic acid construct comprising a first nucleic acid molecule selected from the group comprising:

(a) a nucleic acid molecule having the nucleotide sequence SEQ ID No 3;
(b) a nucleic acid molecule having the nucleotide sequence SEQ ID No 10;
(c) a nucleic acid molecule having the nucleotide sequence of nucleotides 805 to 1221 of SEQ ID No 3;
(d) a nucleic acid molecule having the nucleotide sequence of nucleotides 904 to 1221 of SEQ ID No 3;
(e) a nucleic acid molecule having the nucleotide sequence of nucleotides 1011 to 1221 of SEQ ID No 3;
(f) a nucleic acid molecule having the nucleotide sequence of nucleotides 15 to 622 of SEQ ID No 3;
(g) a nucleic acid molecule having the nucleotide sequence of nucleotides 15 to 409 of SEQ ID No 10,
(h) a nucleic acid molecule having a nucleotide sequence complementary to the nucleic acid molecule of (a), (b), (c), (d), (e), (f) or (g); and
(i) a nucleic acid molecule with at least 80% of homology or at least 150 nucleotides in length to the nucleic acid molecule of (a), (b), (c), (d), (e), (f), (g) or (h), wherein said first nucleic acid molecule is operably linked to a second nucleic acid molecules encoding a protein of interest and a 3' non-translated region. Preferably the nucleic acid molecule is the promoter having the SEQ ID No 3 or SEQ ID No. 10. Also host cells and transgenic plants stably transformed with at least one of the mentioned constructs are provided.

It is a further object of the present invention to provide a method for expressing at least one protein of interest in a host cell, the method comprises the introduction of one of the above mentioned constructs into a host cell and allowing the host cell to produce a protein of interest, wherein the host cell is selected from the group comprising bacterial, fungal, insect, plant and animal cell.

It is a further object of the present invention to provide a method for obtaining a transgenic plant expressing at least one protein of interest, the method comprises the stable transformation of a plant cell or cell culture with one of the above mentioned nucleic acid constructs, and the regeneration of the cells or cell cultures into a whole plant that expresses at least one protein, wherein the transgenic plant is selected from the group comprising a monocot and dicot plant.

It is a further object of the present invention to provide a transgenic plant stably transformed with at least one of the above mentioned constructs, wherein the protein of interest is the transcription factor Hahb-4, having the nucleic acid sequence selected from the group comprising SEQ ID NO:1, SEQ ID NO:2 and fragments thereof, and wherein the plant is selected from the group comprising monocot and dicot plants and said plant is environmental stress tolerant to situations like drought, high salinity, high osmotic pressure and others, and preferably the plant is resistant and tolerant to water deficit. Most preferably, the plant is water stress tolerant by binding the transcription factor Hahb-4 or a functionally active fragment or variant thereof to a dehydration transcription regulating region of the plant and the dehydration transcription regulating region of the plant is a 5'-CAAT(A/T)ATTG-3' DNA sequence (SEQ ID NO:23).

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 1 shows the genomic sequence encoding sunflower Hahb-4 of the invention. The deduced protein sequence of the open reading frame (SEQ ID NO:24) is indicated below the nucleotide sequence (SEQ ID NO:1). The homeodomain is shown in bold; leucines from the leucine zipper are shown in bold and underlined. The lower part of the Figure shows an alignment of the Hd-Zip domain of Hahb-4 (SEQ ID NO:29) with those of Athb-1 (SEQ ID NO: 25), -6 (SEQ ID NO: 26), -7 (SEQ ID NO:27) and -12 (SEQ ID NO:28). Shaded boxes indicate identical amino acids.

FIG. 3 shows time dependence of Hahb-4 induction by water stress in roots, stems and leaves. Seedlings were subjected to water stress during 0.5 or 1 h, or re-hydrated at different times after a 1 h drought treatment. The same filter was hybridized with an rRNA probe as a control for RNA loading and transfer (lower panel).

FIG. 4 shows time dependence of the response of Hahb-4 to ABA. Total RNA (20 μg) was isolated from seedlings that were either untreated, or treated with 100 μM ABA for different times as indicated in each lane. In the lower panel, the same filter was hybridized with an rRNA probe as a control for RNA loading and transfer.

FIG. 5 shows time dependence of Hahb-4 induction by water stress in roots, stems and leaves. RNA was prepared from different organs of control, 30 min (1), 60 min-(2), or 90 min-water-stressed plants (3). The same filters were hybridized with an rRNA probe as a control for RNA loading and transfer (right panels).

FIG. 6 show that ABA and water stress induce the expression of nuclear proteins that specifically bind to the Hahb-4 DNA target sequence. Lane 0, DNA alone; Lane 1, control plants; lane 2, ABA-treated plants; lane 3, water-stressed plants; A and B indicate two different shifted bands observed with nuclear extracts.

FIG. 18 shows the sequence of nucleotides of the promoter region of Hahb-4 gene (SEQ ID NO:3), remarking the sequences corresponding to the TATA box, the element responding to water stress/low temperatures, ABRE regions and the sequences indicating the recognizing sites of Myb and Myc.

DESCRIPTION OF THE PREFERRED EMBODIMENTS

Now referring in detail to the invention, the same refers to the characterization of a new gene Hd-Zip, the sunflower Hahb-4 gene responsive to water stress conditions. Within the homeodomain, Hahb-4 shows a partial homology with Athb-7 and Athb-12, two related proteins from *A. thaliana*. Protein Hahb-4 has the homeodomain located closely to the N-terminal.

The invention discloses a clone from cDNA library. This clone represents a member of the Hd-Zip family that was named Hahb-4. Sequences corresponding to the 5' and 3' ends were obtained by PCR. The complete cDNA sequence obtained in this way is 674 bp long (SEQ ID No 2) and contains an open reading frame of 177 amino acids (FIG. 1).

Comparison of the encoded protein with other Hd-Zip protein sequences indicates that it can be included in the subfamily I of Hd-Zip proteins, sharing about 50% identical amino acids within the homeodomain with other members of this sub-family, with the exception of Athb-7 and Athb-12, that have 60 and 53% identity, respectively, within this region (FIG. 1). It is also noteworthy that the Hahb-4 homeodomain is located almost at the amino terminal end of the protein (amino acids 17-76). As a consequence, Hahb-4 lacks the acidic domain present in other members of the Hd-Zip protein family adjacent to the N-terminal end of the homeodomain. This characteristic is also shared with Athb-7 and Athb-12. In order to investigate the genomic structure of the Hahb-4 gene, we have amplified genomic DNA (genomic DNA is SEQ ID No 1) with several oligonucleotides comprising the entire cDNA. A single intron of 101 bp was detected between nucleotides 381 and 382 (amino acids 108 and 109) of the cDNA.

Northern blot analysis indicated that the Hahb-4 gene of the invention is expressed at very low levels in sunflower plants grown under controlled and normal environmental conditions. Only faint signals were obtained with total RNA extracted from several tissues and developmental stages.

Figure 2:
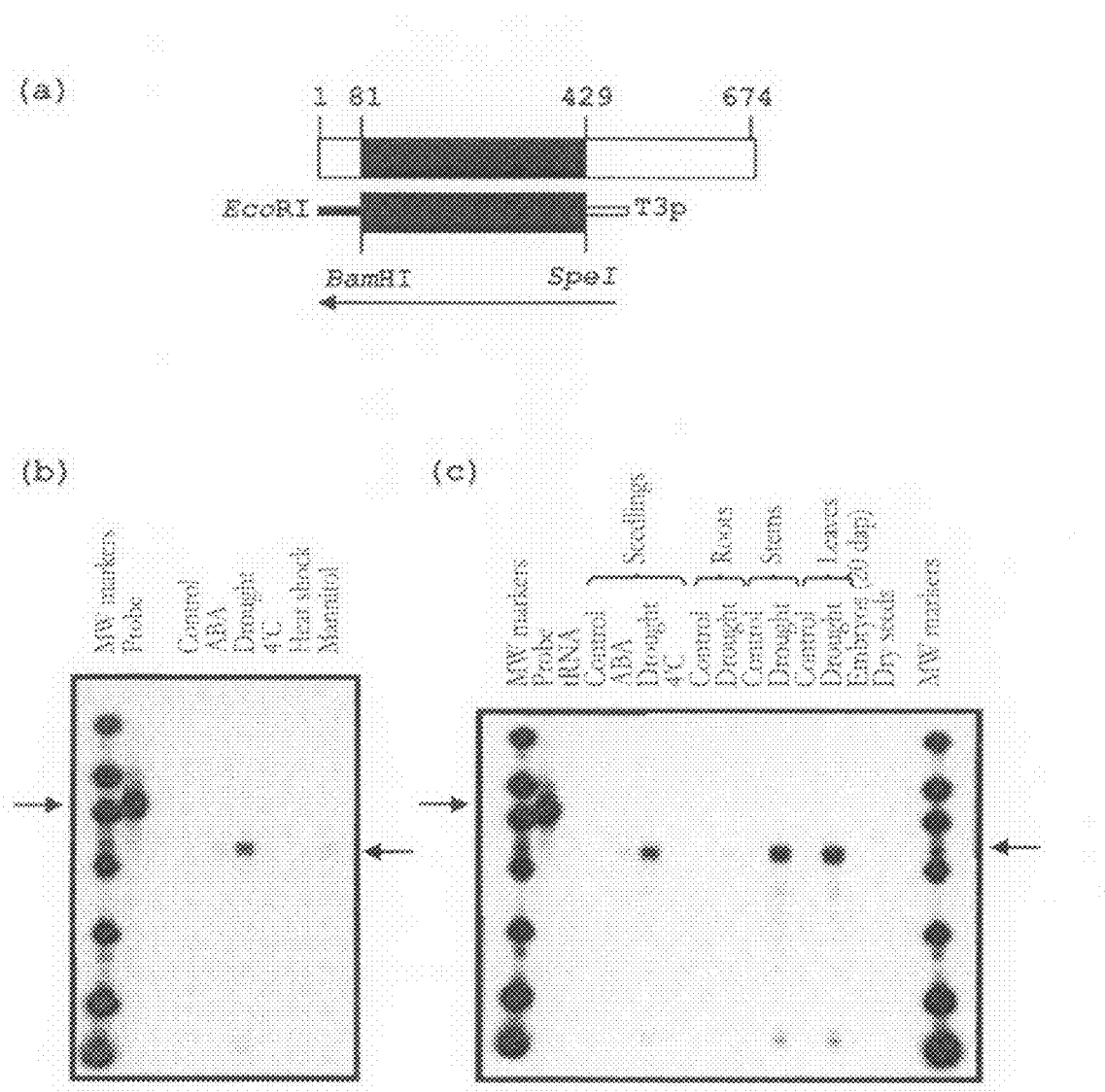
FIG. 2a shows a scheme of the Hahb-4 cDNA showing the length and polarity of the riboprobe (arrow), and the region protected by the Hahb-4 mRNA (+81 to +429; shaded box).
FIG. 2b shows the expression of Hahb-4 induced by water stress subjected to different treatments. Four-day-old seedlings were treated as follows: 100 µM ABA during 24 h; water stress during 2 h; 4° C. during 24 h; 42° C. during 2 h; 0.5 M mannitol during 4 h.
FIG. 2c shows the expression of Hahb-4 induced by water stress in different organs during 2 h, embryos, and dry seeds were analyzed.

We have analyzed the expression of Hahb-4 under different environmental conditions (i.e. water, osmotic, salt, cold, heat, and oxidative stress) by RNAse protection, which is more sensitive than the Northern technique (FIG. 2). FIG. 2b shows that Hahb-4 was not detected in 4-day-old seedlings grown under normal conditions. In water-stressed seedlings, however, a strong signal was observed. Mannitol also induced Hahb-4 expression, although at lower levels, probably reflecting the decrease in water activity caused by this compound (FIG. 2b). A similar result was obtained with NaCl.

As many responses to water stress are mediated by ABA, we have also analyzed the effect of this hormone on the expression. As shown in FIG. 2b, induction was observed after 24 h of treatment of irrigated seedlings with 100 μM ABA. A smaller, but significant increase in transcript levels was also observed with 10 μM ABA. No detectable effect was observed when the seedlings were subjected to either cold (4° C.) or heat (42° C.) stress conditions (FIG. 2b). These results indicate that the effect of water stress is specific.

FIG. 2c shows that the response to water stress conditions is also observed in roots, stems, and leaves of older (21-day-old) plants. The level of induction in aerial parts of the plant is similar to that observed in seedlings. Roots, on the contrary, show considerably lower transcript levels under water stress conditions.

Since ABA also participates in seed development during late embryogenesis, which involves a desiccation process, we analyzed Hahb-4 transcript levels in sunflower embryos (20 d after pollination) and in dry seeds. No signal was obtained in RNAse protection experiments (FIG. 2c), indicating that the response of Hahb-4 to water stress and ABA is characteristic of vegetative phases of development.

The high level of induction observed under water stress conditions allowed us to analyze the time-dependent increase in transcript levels by Northern experiments. FIG. 3 shows that seedlings exposed to drought significantly increased their Hahb-4 transcript levels after only 30 min; the response reached a maximum after 1 h of withholding water. After this time, no further increments in Hahb-4 transcript levels were observed. Re-hydration of the seedlings lowered Hahb-4 transcript levels more slowly, with only about a 50% decrease after 2 h (FIG. 3, lanes 4 and 5). The effect of ABA treatment was also time dependent. As shown in FIG. 4, the response to ABA was detectable within 1 h and reached a maximum after 3-6 h. After that, transcript levels decreased slowly, but were still significantly high after 24 h of treatment. The high Hahb-4 transcript levels of the invention are reverted after the re-hydration of the sunflower plants, thus indicating again that said gene participates in the response to the water stress.

The response of Hahb-4 to water stress in different organs of hydroponically grown 3-week-old plants was also rapid. In roots, transcript levels reached a maximum after 60 min. of stress treatment (FIG. 5).

In leaves and stems, a maximum response was observed after more prolonged treatments. This may be related to the fact that the initial perception of water stress is accomplished by the root, which synthesizes ABA that is then translocated to aerial parts of the plant. This, together with the results previously shown in FIGS. 2-4, most likely indicates that Hahb-4 expression is related to endogenous ABA levels in water-stressed plants.

The presence of functional DNA binding proteins in sunflower nuclei was analyzed by electrophoretic mobility shift assays using a synthetic double-stranded oligonucleotide comprising the sequence 5'-CAAT(A/T)ATTG-3', bound in vitro by Hahb-4 expressed in bacteria. Nuclear extracts prepared from 4-day-old seedlings showed distinct shifted bands, indicating the existence of at least two different protein complexes that bind to this sequence (FIG. 6). The amount of both complexes was significantly increased in extracts obtained from ABA-treated plants. On the contrary, only the slower-migrating complex increased when plants were subjected to water stress. Formation of both complexes was almost completely abolished by an excess of the same unlabelled DNA, but not by an equivalent amount of a similar DNA containing the sequence 5'-CA<u>C</u>T(A/T)A<u>G</u>TG-3' (changed positions underlined) not bound by Hahb-4 (FIG. 6). This result strongly suggests that at least one functional protein with the same DNA-binding specificity as Hahb-4 is synthesized and translocated to the nucleus in the presence of ABA or under water stress conditions.

The intense Hahb-4 expression was detected only in plants subjected to a water stress or to a treatment with ABA. Heat, cold and oxidative stress do not induce such expression. The salts and the osmotic treatments only produce small increments in Hahb-4 transcription levels. The water stress effect was entirely reversed when the plants were re-hydrated. These characteristics suggest that the inventive Hahb-4 expression directly responds to the hydric status of the vegetal cells and that the induction is not an effect from damage or general stress.

Figure 7:
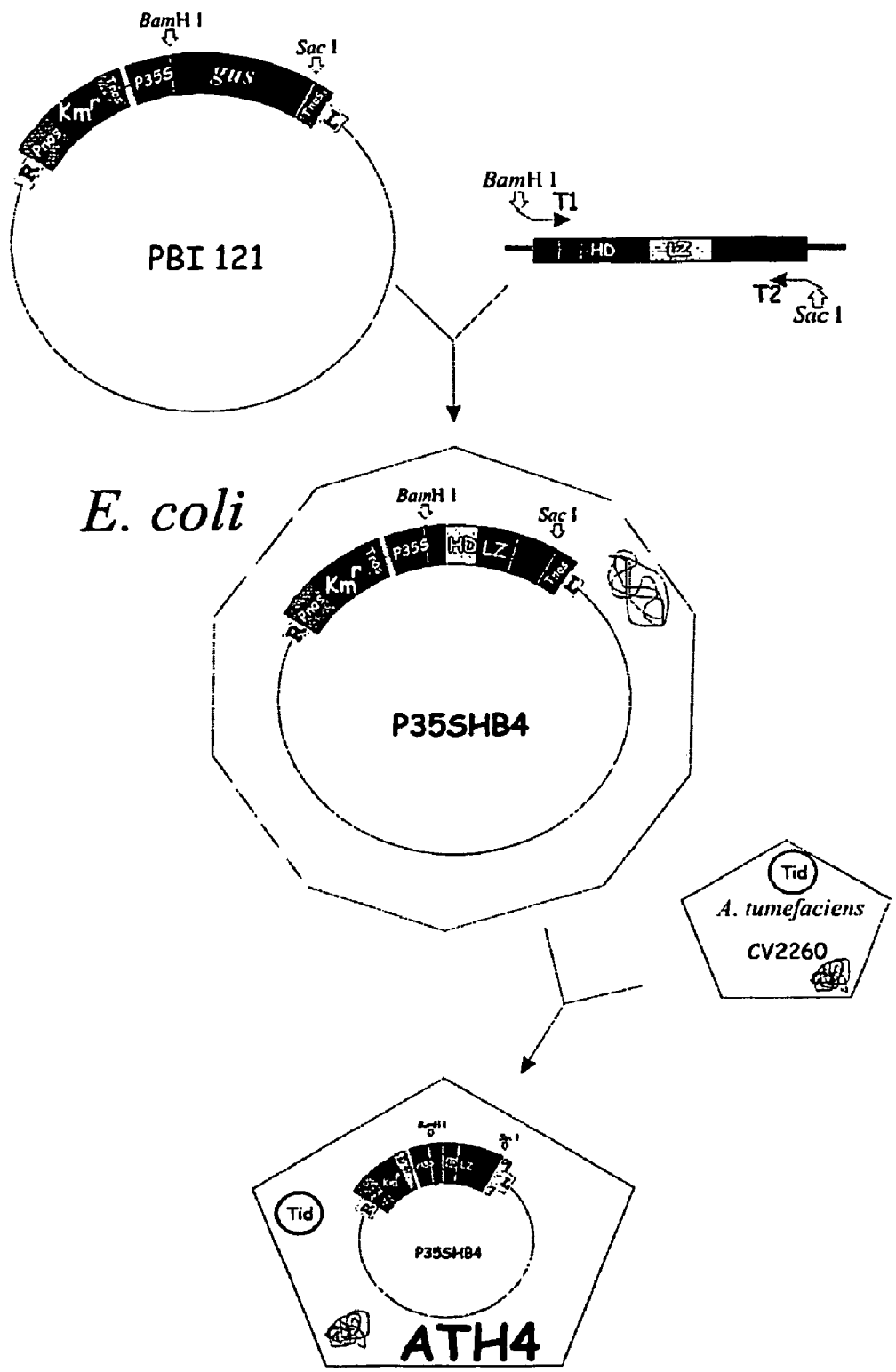
FIG. 7 shows a graph illustrating the strategy employed for cloning the cDNA encoding Hahb-4 under the control of CaMV35S promoter. Plasmid p35SHB4 was constructed in *E. coli* and then it was used for transforming strain CV2260 of *A. tumefaciens*. Strain *A. tumefaciens* having the plasmid containing Hahb-4 cDNA under the control of CaMV35S promoter was named ATH4. BD y BI: right and left edges; Pnos: nopaline synthetase gene promoter; Tnos: termination sequence of nopaline synthetase; $Km^r$: kanamycin resistance gene; P35S: 35ScaMV promoter, gus: β-glucuronidase gene.

For obtaining transgenic plants of *Arabidopsis thaliana* that over-express sunflower Hahb-4 of the invention, the vector pBI121 and the "floral dip" method were used, as disclosed in Example 3 and FIG. 7. As a result, many independent lines of transgenic plants have been obtained wherein the plants were tolerant or resistant to growth in a medium with kanamycin as PCR positive reaction with specific oligonucleotides. From the obtained independent lines, those having a transgene stable expression (the Hahb-4 gene of the present invention) were selected. Subsequently, the homozygotes lines F3 were selected to analyze the phenotype.

Figure 8:
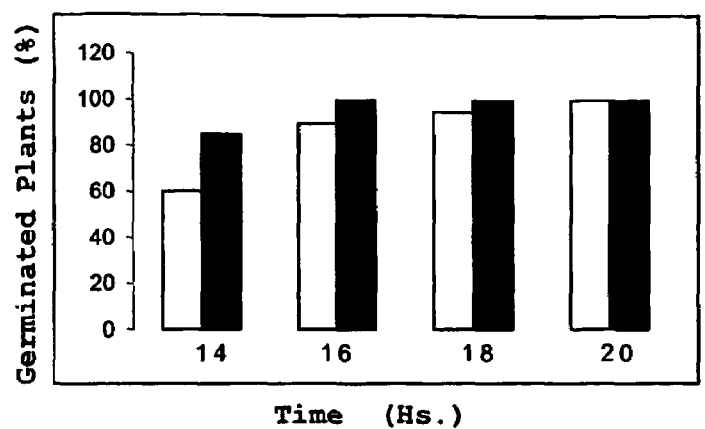
FIG. 8 is a graph showing the germination time of the inventive transformed plant (dark bars) and the untransformed control plants (white bars) in percentage of germinated plants after a 48 treatment at 4° C. (n=22).

As it is shown in FIG. 8, the *A. thaliana* transgenic plants carrying the inventive gene germinates more rapidly as compared to the non transformed control plants. After 14 hours, 85% of the transformed plants according to the invention germinated vs. the 58% of non transformed ones.

Figure 9:
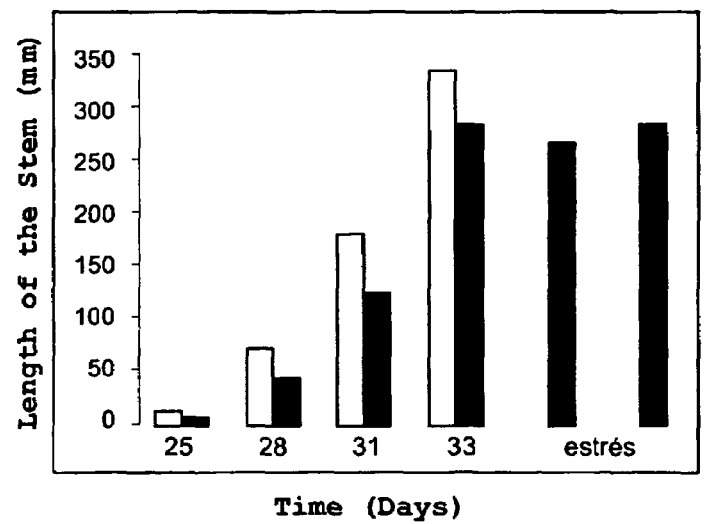
FIG. 9 is a graph showing the length of the stem measured in mm of the inventive transformed plants (dark bars) and the non transformed control plants (white bars) from the 28 days to 33 days since germination. The two end bars show the stem length of transgenic plants subject to water stress tests wherein there were no survivors in the group of control plants.

In addition, the stems of the inventive transformed plants enlarges more slowly and reach a maximum height that is equivalent to the 85% of the height of a control plant that was grown in the same conditions (with normal water availability—FIG. 9). In addition, the transgenic plants subjected to water stress reached a stem height similar to the one of the same transgenic plants grown with normal water availability, thus indicating that the water stress does not affect the stem growth in the transgenic plants of the invention (FIG. 9). The inventive transgenic plants are not only tolerant to the water stress but also they normally growth in lack-of-water conditions, without important alterations in the observed phenotype.

Figure 10:
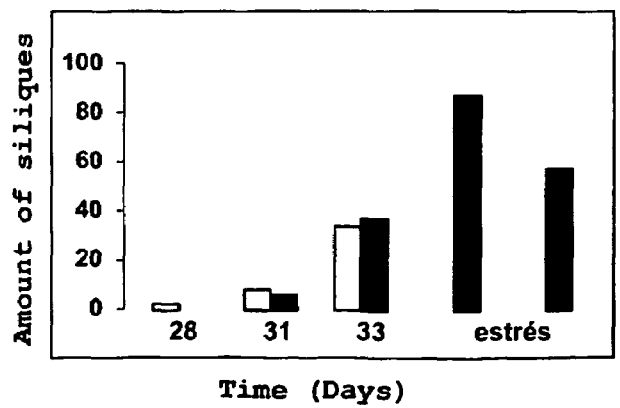
FIG. 10 is a bar graph showing the amount of siliques formed during the development of the plants, non transformed control (white bars) and transgenic plants (dark bars). The two end bars show the quantity of siliques of transgenic plants subject to water stress tests wherein there were no survivors in the control plants group. This plants were irrigated at the end of the cycle and once recuperated the parameters of interest were recorded.

The number of formed siliques did not significantly vary between wild type and transgenic plants and this number is slightly higher in the transgenic plants in spite of the shortening of the floral pedicel (FIG. 10). When the transgenic plants grown under water stress conditions are compared with the same plants grown in normal conditions, the number of formed siliques is higher in those subjected to stress (FIG. 10). In addition; as it is shown in Table 1, the total weight of the seeds produced by plants transformed according to the invention was about 15% higher compared with that of the seeds from control non transformed plants.

TABLE 1

|  | Transgenic Plants | Control Plants |
| --- | --- | --- |
| Average seed weight | 0.0964 | 0.0803 |
| SD | 0.0350 | 0.0224 |
| Number of Plants | 12 | 12 |

Since the Hahb-4 product acts as a transcription factor and its expression at a the transcription level seems to be regulated by the availability or presence/absence of water, studies have been performed for to determine the tolerance to water stress in transformed plants over-expressing the sunflower Hahb-4 gene of the invention.

Figure 11:
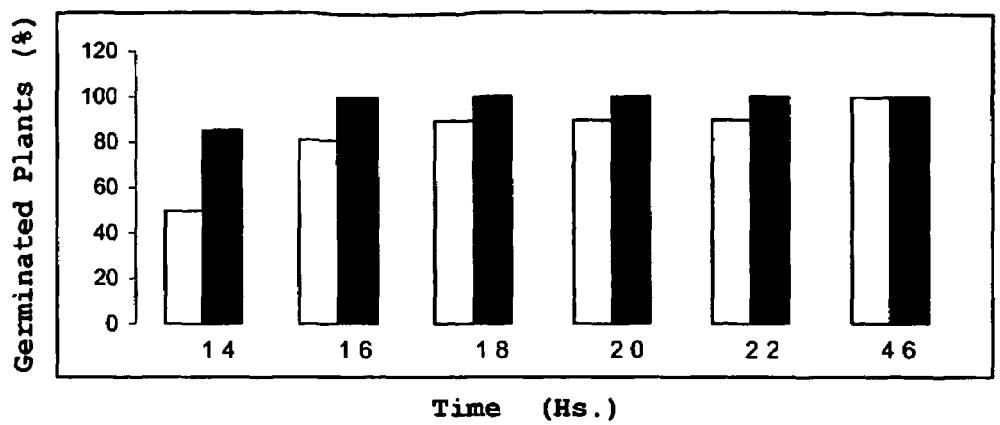
FIG. 11 is a bar graph showing the percentage of non transformed control (white bars) and transgenic plants (dark bars) germinated at different times after breaking the dormancy in the presence of 50 mM mannitol.
Figure 12:
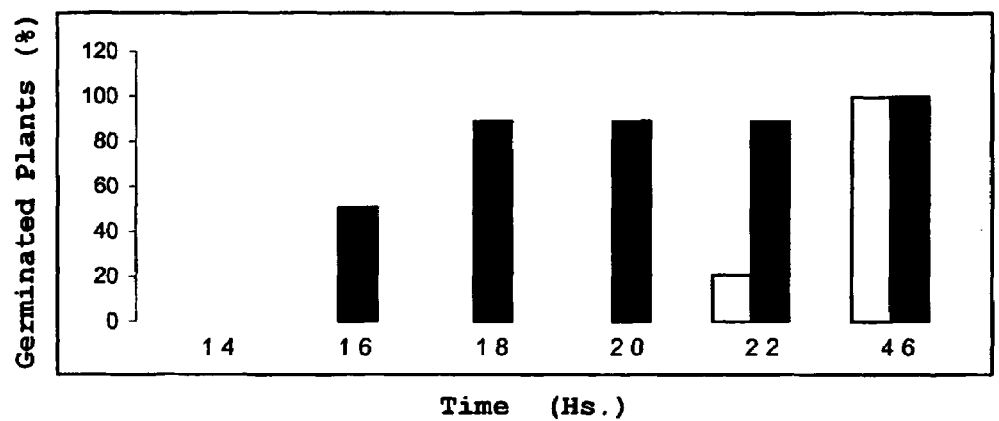
FIG. 12 is a bar graph showing the percentage of non transformed control (white bars) and transgenic plants (dark bars) germinated at different times after breaking the dormancy in the presence of 200 mM mannitol.
Figure 13:
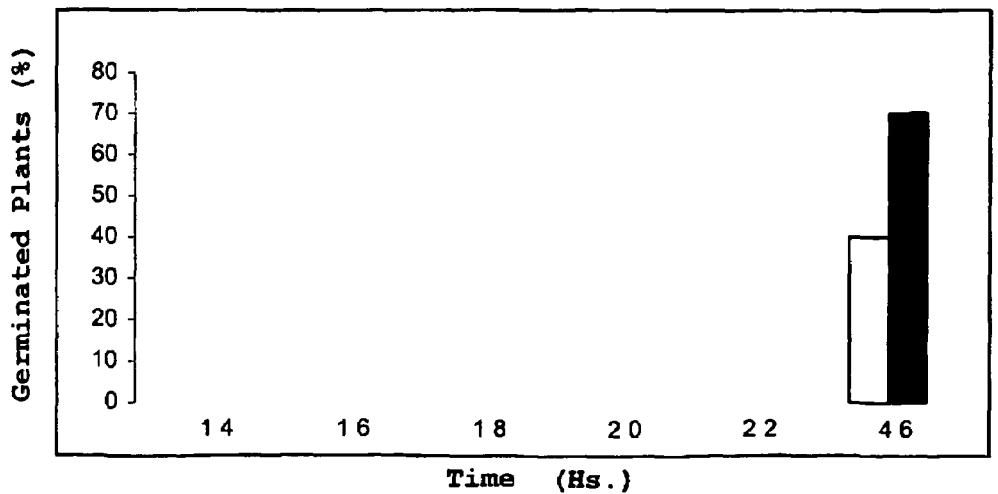
FIG. 13 is a bar graph showing the percentage of non transformed control (white bars) and transgenic plants (dark bars) germinated at different times after breaking the dormancy in the presence of 300 mM mannitol.

First, the germination process, under conditions imitating the lack of water, such as presence of mannitol, and other conditions generating salt stress, was analyzed. FIGS. 11, 12 and 13 show the germination times of plants transformed according to the invention as compared to control ones. The presence of mannitol delays the germination. This effect is more remarked at higher concentrations of the carbohydrate. However, the transformed plants keep a good germination efficiency even at high concentrations of mannitol.

Figure 14:
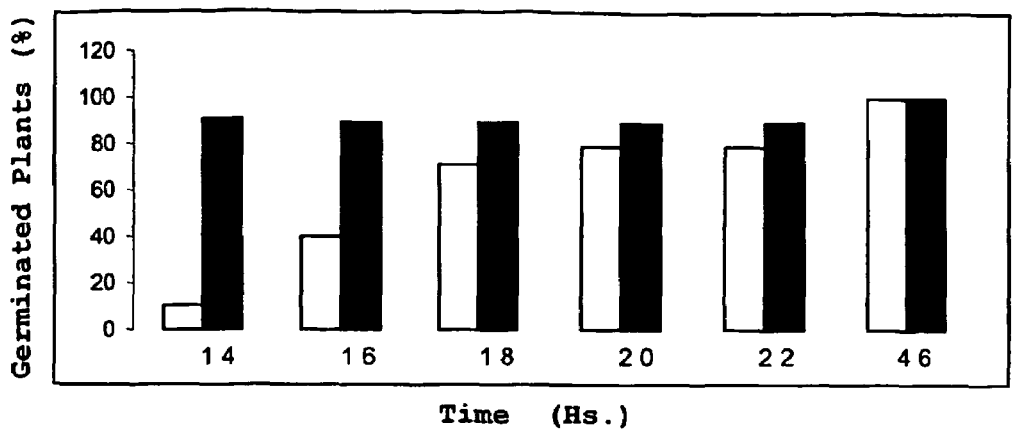
FIG. 14 is a bar graph showing the percentage of non transformed control (white bars) and transgenic plants (dark bars) germinated at different times after breaking the dormancy in the presence of 50 mM NaCl.
Figure 15:
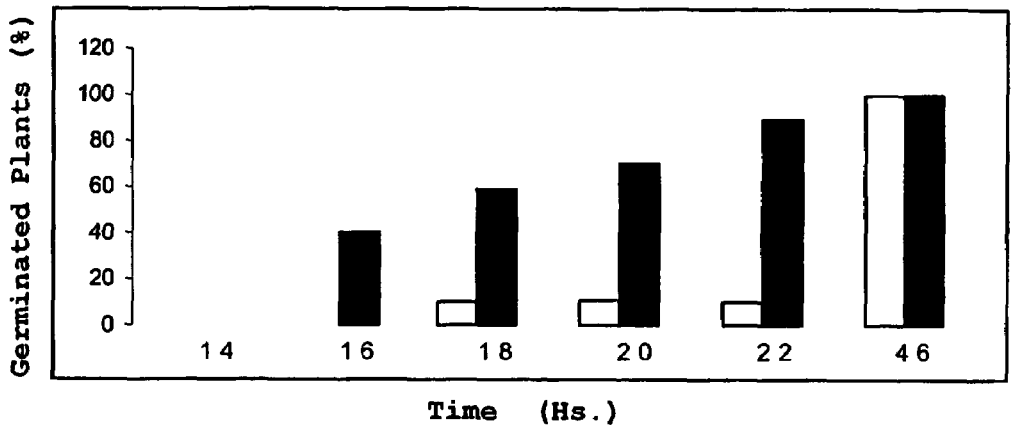
FIG. 15 is a bar graph showing the percentage of non transformed control (white bars) and transgenic plants (dark bars) germinated at different times after breaking the dormancy in presence of 150 mM NaCl.

When the germination tests were carried out in the presence of different concentrations of NaCl the obtained results were similar as in the case of mannitol. As can be seen in FIGS. 14 and 15, the over-expression Hahb-4 provides the transformed plants with a higher germination capacity in a saline medium.

It is to be remarked that the roots of the transgenic plants grown in the different stress conditions tested or assayed are larger than the roots of the control plants, thus indicating a phenotype that provides tolerance to several stress conditions.

Figure 16:
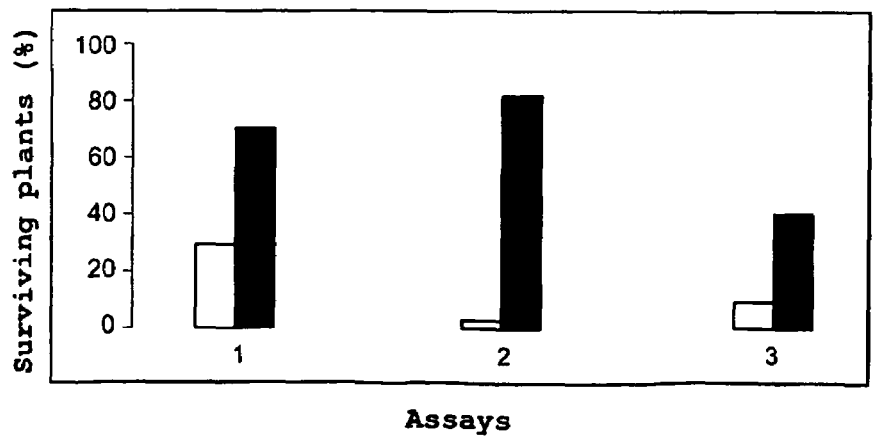
FIG. 16 is a bar graph showing the percentage of non transformed control surviving plants (white bars) and transgenic plants (dark bars) in three independent tests. In the first test (1) the stress occurred when the plants were adult (reproductive stage). In the second test (2) the plants were in advanced vegetative stage (complete rosette). In the third test (3) the stress occurred at the germination.

Subsequently, drought tests have been performed at several plant developmental stages cultured in soil. FIG. 16 shows three tests that show survival to water stress. Clearly, a higher tolerance to water stress in the inventive transformed plants is observed when compared to control non transformed plants.

Figure 17:
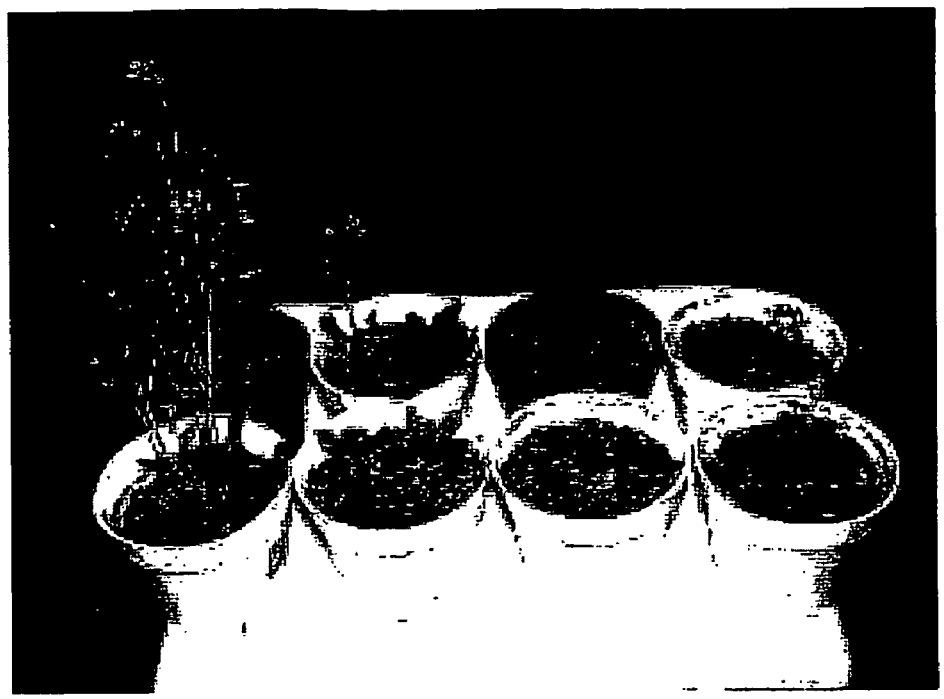
FIG. 17 shows the phenotypes of control and transgenic plants. (a) the phenotype of transgenic plants (1st and 2nd rows) and of non transformed control plants (3rd y 4th rows) is observable. These plants were subjected to water stress when adult and re-irrigated at the end of the life cycle. In b the phenotype of transgenic (left side) and non transformed control plants (right side) is observable. This group of plants was subjected to water stress when they were in vegetative stage. In c the phenotype of transgenic (left side) and non transformed control plants (right side) subjected to water stress since the germination and then re-irrigated is observable. (d) In d is shown the phenotype of transgenic plants subjected to extreme drought at the vegetative stage.
Figure 17:
Figure 17:
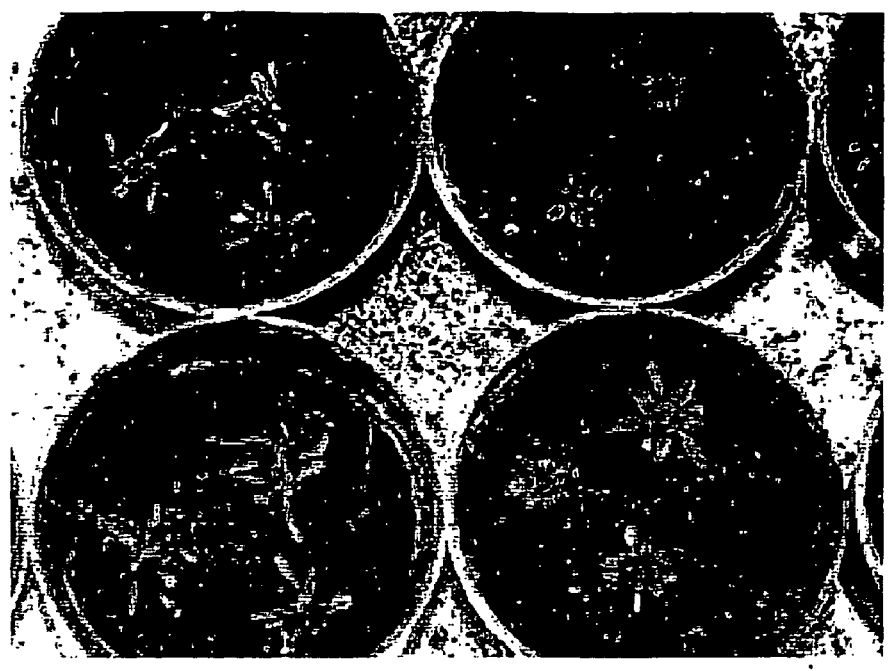
Figure 17D:

When the plants were subjected to water stress at different developmental stages, the transformed ones shown a higher tolerance to stress conditions. FIG. 17 shows the plant status after they have been subjected to lack-of-water conditions at different stages of growth. Whatever the stage is wherein the plant is subjected to water stress, the transgenic ones carrying the inventive Hahb-4 gene are more tolerant and resistant to the above mentioned conditions.

Briefly, the present invention discloses the obtaining of *Arabidopsis thaliana* transformed plants that over-express the sunflower gene Hahb-4 of the invention under the control of 35S cauliflower mosaic virus promoter, the construction shown in FIG. 7. The inventive gene, initially isolated from sunflower, encodes a Hd-Zip protein having a proteic domain of the type homeodomain associated to a leucine-zipper. The experts in the art know that any promoter or construction of nucleic acid driving the expression of the inventive gene may be employed without altering the spirit and scope of the invention. Even more, nucleic acid constructions permitting the expression of the inventive gene in any host cell, such as bacteria, yeast, fungus, animal and vegetal cells, may be prepared. In a preferred embodiment of the invention, the gene expresses in plants cells and tissues.

The transformed plants expressing Hahb-4 have, in normal growing conditions, in average, shorter stems. It seems that this characteristic is mainly due to the inhibition of cellular expansion and not to the inhibition of cellular division, as indicate hystological studies.

In addition to the foregoing, the adult leaves of the transgenic plants are more rounded and less elongated as compared to those of non transformed plants. Both characteristics altogether seem to indicate that the gene product is acting as an inhibitor of the cellular expansion and elongation. These phenotypic characteristics (short stem and round leaf) would be directly related to the capacity of the transgenic plants to tolerate and resist the scarcity or lack of water, as a mechanism for "saving water". On the contrary, the roots of the inventive transgenic plants are longer as compared to the roots of non transformed plants. This would indicate the presence of another advantageous mechanism for obtaining water.

The transgenic plants of the present invention are markedly tolerant to water stress in different growing stages, either in the germination as well as in the early and end vegetative periods, and also in the reproductive period. The survival percentage of transgenic plants is higher than the one observed for the non transformed control plants when both are subjected to drought conditions.

With all these results we may conclude that the Hahb-4 gene is involved in the plant response to water stress and that its specific function would be to generate phenotypic changes enhancing the tolerance of the plant to the lack of water.

Remarkably, none of these phenotypic changes negatively affects the production and germination of the plants. On the contrary, the seeds production (measured in weight) of the transgenic plants is higher than the production of non transformed plants.

The Hahb-4 of the invention may be employed for producing transgenic plants having a commercial interest wherein said transgenic plants have characteristic tolerances to water stress. It may be expected that the productivity of said agronomic valued plants subjected to water stress is similar to the productivity of the variety that is non transformed and not subjected to such stress conditions. As an example, such agronomic valued plants may include, but are not restricted to, sunflower, wheat, barley, soybean, potato, corn, sugar cane or rice.

It is important to remark that there is not a large variety of genes that over-expresses when the plant is subjected to water stress and there is no concrete evidence that said genes could provide a plant with tolerance to drought like the inventive Hahb-4 does.

The inventors have isolated and characterized the sequence of the promoting region of sunflower Hahb-4 according to the invention. The isolation of Hahb-4 promoting region was carried out in three stages by inverse PCR technique, using the information obtained in a one stage for designing the new pair of oligonucleotides to be used in the next. The obtained fragments from the PCR reaction were cloned into pGEM.-T easy vector (Promega), and the sequence of the promoting region was manually completed by overlapping the repeated regions of each construction.

The sequence of Hahb-4 (SEQ ID No 3) promoter corresponds to a 1221 pb sequence, comprising a TATA box located 24 pb upstream of the transcription initiation site. The comparison of this sequence with the ones existing in the data bases, reveals the existence of regions with homology to sequences thought to be involved in the response to several environmental factors, such as light, abscisic acid and hormones. As an example, FIG. 18 shows putative elements responding to ABA of the type ABRE as well as an element that responds to the drought stress or low temperatures of the type DRE.

The consensus sequences of the transcription factor joint involved in the response to transcription factors, such as the proteins of the families Myb y Myc (Abe et al., Plant cell 9: 1859-1868, 1997; Shinozaki and Yamaguchi-Shinozaki, Plant Physol. 115: 327-334, 1997, herein incorporated as references) were also identified.

After the isolation and sequencing of Hahb-4 promoter the sequences involved in the driving of the gene expression were sought for. Particularly, providing organ specificity and the sequences responding to water stress and the presence of ABA. For this purpose plants of *A. thaliana* with constructions comprising a reporter gene (gus gene) were transformed under the control of the total sequence of said promoter or parts of said sequence.

The complete sequence of the promoter was cloned in one construct. For this purpose two specific oligonucleotides that hybridized in the ends of the promoting region were designed, and they were employed in a PCR reaction by using sunflower genomic DNA as template. As a product of the amplification reactions two bands of about 1000 and 1200 bp were obtained. Considering that the vegetal material used for these tests was isolated from a hybrid (contiflor 15), the presence of two bands seems to indicate the existence of two different alleles present in the genome.

Figure 19:
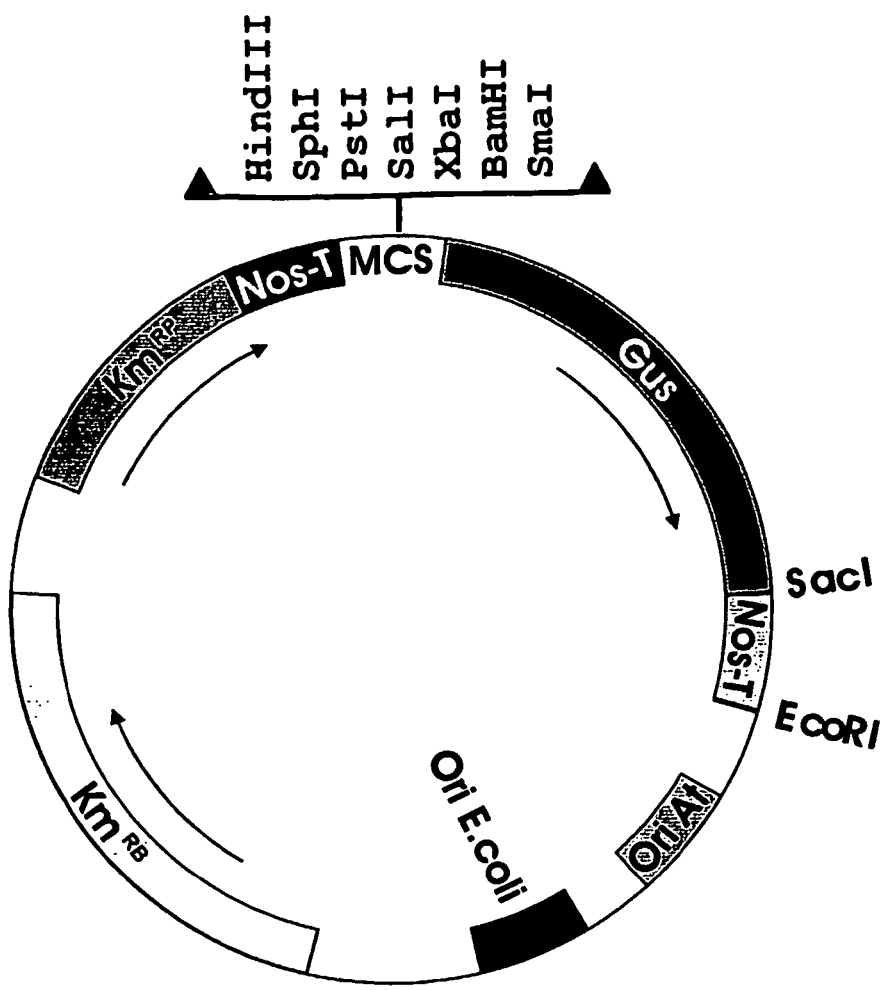
FIG. 19 shows an scheme of pBI 101.3 vector used for cloning several segments of the Hahb-4 promoter. β-glucuronidase gene is indicated, as well as the genes providing resistance to kanamycin in *E. coli* and *A. tumefaciens*. The replication origins of *E. coli* and *A. tumefaciens* are also marked.

Both PCR products were cloned into pGEM-Teasy vector (Promega). Then they were restricted with BamHI and HindIII and cloned into pBI101.3 vector (FIG. 19) as it is indicated in Example 4. Two constructs, each comprising one of the alleles of the promoter, were obtained, wherein said promoter alleles drive the expression of gus gene.

Subsequently, different fragments of the promoter including the transcription initiation site were cloned into pBI101.3 vector. For cloning the promoter segments that are more distant from the transcription initiation site a modified pBI vector was utilized, the vector carries a minimal promoter (–90 CaMV35S) including the TATA box. The obtained clones are described as follows:

Clone 416: fragment containing the region from 0 to –400 (from the transcription initiation site up to IPCR4 (SEQ ID No 4)) of the promoter cloned into pBI101.3 HindIII/BamHI. Clone 416 comprises the nucleotides 805 to 1221 of SEQ ID No 3.

Clone 1015: fragment containing the promoting region from 0 to –1015 (small allele) obtained with the nucleotides IPCR10 and IPCR8 (SEQ ID No 5 and SEQ ID No 6, respectively) cloned in SalI/BamHI of pBI101.3.

Clone 1221: fragment containing the promoting region from 0 a –1221 (large allele) obtained with the oligonucleotides IPCR10 e IPCR8 (SEQ ID NO 5 and SEQ ID No 6, respectively) cloned in SalI/BamHI of pBI101.3.

Clone 318: fragment containing the region from 0 to –300 (from the transcription initiation site up to IPCR6 (SEQ ID NO 7) amplified with the oligonucleotides IPCR6/IPCR8 (SEQ ID NO 7/SEQ ID NO 6)) of the promoter cloned in HindIII/BamHI of pBI101.3. Clone 318 comprises the nucleotides 904 to 1221 of SEQ ID NO 3.

Clone 211: fragment containing the region from 0 to –211 (from the transcription initiation site up to IPCR7 (SEQ ID No 8) amplified with the oligonucleotides IPCR7/IPCR8 (SEQ ID No 8/SEQ ID NO 6) of the promoter cloned in HindIII/BamHI of pBI101.3. Clone 211 comprises the nucleotides 1011 to 1221 of SEQ ID No 3.

Clone 608: fragment of 608 pb (from the large allele) corresponding to 5' promoter region (amplified with IPCR5/IPCR10 (SEQ ID No 9/SEQ ID NO 5)) cloned in SalI of pBI –90 with a minimal promoter. Clone 608 comprises the nucleotides 15 to 622 of SEQ ID No 3.

Clone 407: fragment of 407 pb (from the small allele) corresponding to the 5' promoter region (amplified with IPCR5/IPCR10(SEQ ID No 9/SEQ ID No 5)) cloned in SalI of pBI –90 with a minimal promoter. Clone 407 comprises the nucleotides 15 to 409 of SEQ ID No 10.

Subsequently, plants of *A. thaliana* were transformed with the above mentioned constructs, the transformed plants were selected and several independent lines were chosen for isolating, in the third generation, homozygote sub-lines. The selected homozygote plants were used for characterizing the alleles and the different regions of the Hahb-4 promoter by hystochemistry and fluorimetry tests.

The region 0 to –400 of the promoter was enough to drive the expression of gene gus in cotyledons of 2-day germination seedlings. Such expression was not detectable in the young seedlings at the 10 germination days.

Figure 20:
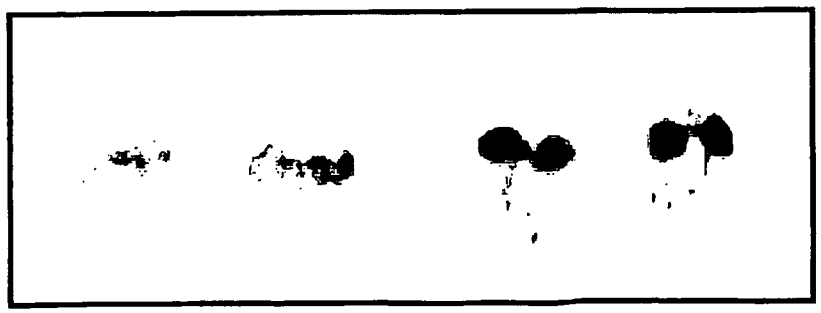
FIG. 20 shows a photograph comparing the expression levels measured by hystochemistry of gene gus in 10-day old seedlings carrying the constructs of promoter of 0 to −400 sequence (nucleotides 805 to 1221 of SEQ ID No 3) (left side) and 0 to −1015 sequence (small allele) (right side).

When the construct including the complete segment of the small allele was employed, the expression of the gus gene in the cotyledons of 2-day germination seedlings was also viewed. However, and differing from the region 0 to –400, the expression of gus gene was very intense in the leaves and roots of the young seedlings (FIG. 20). Finally, it was not detected any expression of gus gene in the plants during the reproductive stage.

These results indicate that while the expression occurs in the same organ or organs, the intensity of such expression is different. It is possible that in the region –400 to –1015 important sequences for transcription activation may be present, while the sequences necessary for driving the specific expression in cotyledons and leaves are in the region 0 to –400.

Figure 21:
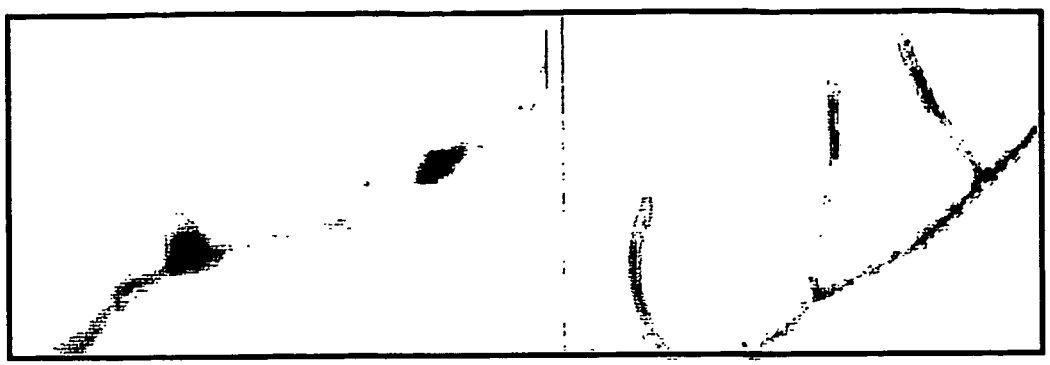
FIG. 21 shows the expression of gus in the roots of *A. thaliana*. (a) shows the expression of gene gus in 20-day old roots of plants transformed with construct of 0 to −400. (b) shows the expression of gene gus in 20-day old roots of plants transformed with construct of 0 to −1015. (c) shows the expression of gene gus in 10-day old roots of plants transformed with construct of 0 to −1015.
Figure 21:
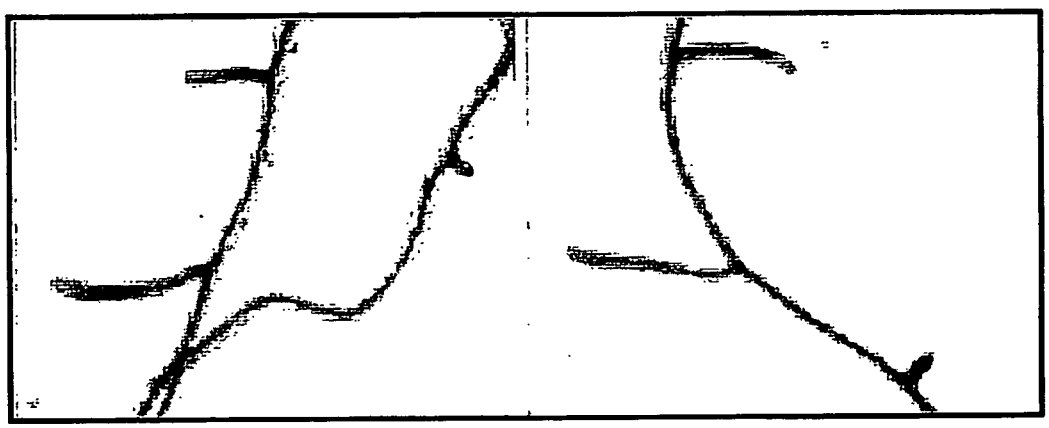
Figure 21:

When the expression of gus gene in the roots of the transgenic plants was analyzed, it has been found that the expression driven by the construct 0 to –400 in the roots of 20-day old plants is consistently more strong in the lateral roots primordium and in the intermediate region of the lateral roots already developed. In addition, it was viewed that in the roots of the transformed transgenic plants with the construct of 0 to –400, the expression of the gus gene is also detectable in cells of the vascular cylinder (FIG. 21). 10 days after germination a strong expression in all the main and lateral root, and even stronger in the region of the roots base (FIG. 21*c*) is observed.

Figure 22:
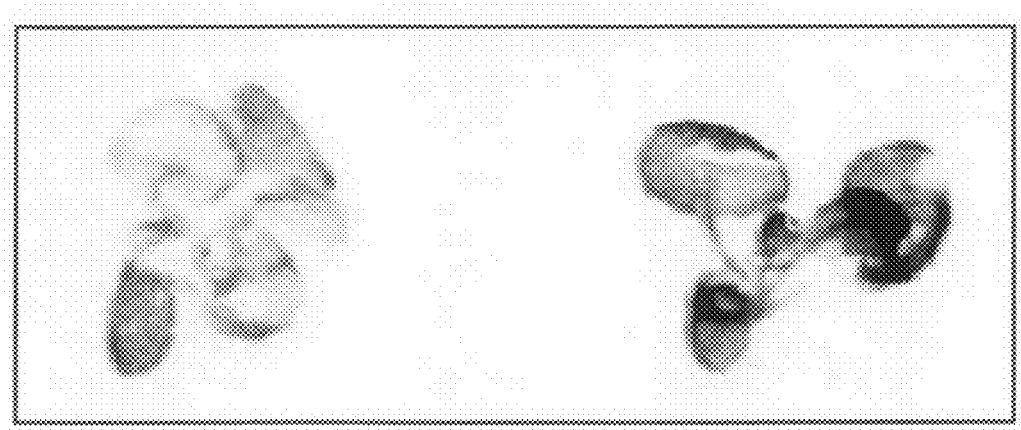
FIG. 22 shows the effect of ABA treatment in 20-day old seedlings transformed with the construct 0 to −400. At the left side the control plant is shown and at the right side the seedling treated with ABA is shown.

The results obtained by fluorimetry tests shown that the construct including the complete segment has a promoting activity 10 times higher than the promoting activity of the construct 0 to −400. Also, the construct 0 to −400 is capable of being induced by ABA, as it is shown in FIG. 22.

The analysis of several independent lines of plants transformed with the constructs comprising the region 0 to −300 or the region 0 to −200 shown that the gus gene is not expressed in the different development stages, in none of the studied organs, and said promoting regions are not induced by ABA.

The inventors also disclose the presence of only one intron that interrupts the region of the leucine-zipper encoding sequence. This intron has 101 pb and is located specifically between the sequences encoding the sixth and seventh heptade of the leucine-zipper domain (aminoacids 108 and 109) and responds to rule 5'-GT . . . AG-3' present in the introns of other organisms. A scheme of location and sequence of the intron is shown in FIG. 1.

Therefore, the present invention comprises the Hahb-4 promoter (SEQ ID No 1) and the cDNA of said gene (SEQ ID No 2), wherein said gene encodes a protein of the sunflower Hd-Zip family. The promoter has two alleles that were cloned and sequenced, having a divergent or not conserved region around the nucleotide −900. The large allele comprises a sequence of 1221 bp and the small allele comprises a sequence of 1015 pb (SEQ ID NO 3 and SEQ ID NO 10, respectively).

The analysis of the promoter nucleotide sequences indicated that there are regions homologous to different sequences involved in the response to several environmental factors such light, abscisic acid and hormones. The promoter of the invention comprises putative elements responsive to ABA commonly named ABRE as well as an element responsive to stress produced by lack of water or low temperatures called DRE. The consensus sequences joining the transcription factors involved in the response to environmental factors were also identified.

When the activity of different regions of the inventive promoter was analyzed, the obtained results indicated that while there are two putative elements ABRE between the transcription initiation site and 300 nucleotides upstream, this segment is not capable to drive the reporter gus activity, showing that this segment, while necessary, is not enough to activate the transcription. On the contrary, by taking the first 400 nucleotides adjacent the position +1, the expression of gus gene in cotyledons after 2-days germination and in roots has been observed. The expression is not very strong but it is specific and capable to be induced by ABA.

On the other hand, the complete segment of the promoting region produces expression levels that are at least 10 times higher than the levels generated by the segment 0 to −400. In turn, this expression is evident in older stages of the development (plants of up to 20 days of germination) and in the central region of the root.

The inventive promoter (both alleles) and the segments or parts thereof may be employed for driving the expression of any gene of interest. Preferably, the promoter of the invention (both alleles or segments thereof) may be employed in nucleic acid constructs useful to transform host cells, wherein said promoter drives the expression of any protein of interest. The host cells may be bacteria, yeast, animal cells or vegetal cells.

Also a vector may be constructed wherein the inventive promoter drives the expression of the Hahb-4 gene of the invention in vegetal cells. Said constructions are useful for obtaining transgenic plants that are tolerant to water stress. The transgenic plants carrying the Hahb-4 gene of the invention and the promoter of the invention may be commercial plants including, while not restricted to, sunflower, wheat, barley, soybean, potato, corn, sugar cane or rice.

The invention may be better understood with reference to the following examples which are not limitative or restrictive of the scope of protection. On the contrary, it must be clearly understood that many other embodiments, modifications and alterations equivalent to the elements of the invention may be suggested by persons skilled in the art after reading the present description, without departing from the spirit of the present invention and/or the scope of the appended claims.

EXAMPLES

Example 1

Isolation and Characterization of the New Sunflower Gene Hahb-4, that is a Gene Encoding a Protein Belonging to the Hd-Zip I Family A. Hahb-4 Gene cDNA Isolation:

For the isolation of partial cDNA clones containing homeobox sequences, a polymerase chain reaction (PCR)-based strategy was carried out as previously described (González and Chan, Trends in Genetics 9:231-232, 1993, herein incorporated as reference) on total DNA from a sunflower stem cDNA library constructed in lambda gt10. Sequences representing the 3'end of the Hahb-4 transcript were obtained by PCR using lambda gt10 sequencing primers and the specific primer H41 (5'-GGCGGATCCAACA-GAAACAACCACCAGG-3' (SEQ ID No 11)), that matches nucleotides 81-100 of the cDNA sequence (SEQ ID No 2 and FIG. 1). The 5'-end of the transcript was obtained applying rapid amplification of cDNA ends (RACE) to polyA+RNA obtained from water-stressed sunflower stems using the specific oligonucleotide IPCR0 5'-GGCGGATCCCCTGGTG-GTTGTTTCTGTT-3' (SEQ ID No 12) and primers Qt and Qo (SEQ ID No 13 and SEQ ID No 14, respectively) according to Frohman (Frohman Cloning PCR products. In The Polymerase Chain Reaction, eds. K. B. Mullis, F. Fré, & R. A. Gibas, pages 14-37. Birkhauser, Boston, Mass., USA, 1994, herein incorporated as reference).

B. Isolation of Hahb-4 Genomic Sequence:

The 5'non-transcribed region of Hahb-4 was characterized using inverse PCR according to Ochman, Ayala & Hartl (In Methods of Enzymology (ed R. Wu) Vol 218, pages 309-321. Academic Press, San Diego, Calif. USA, 1993). Sunflower genomic DNA was partially digested under controlled conditions with Sau3A or HindIII. Circularization of DNA after digestion and purification was carried out overnight in the presence of 5 U of T4 DNA ligase (PromegaCorp., Madison, Wis., USA) according to the manufacturer's instructions. Primer pairs used for amplification were 5'-GGCGGATC-CCCTGGTGGTTGTTTCTGTT-3'(SEQ ID No 12) and 5'-GCCGAATTCAGATTGAGCAAGAGTATAAC-3' (SEQ ID No 15), or 5-ACCTTTATAAAGACCACTC-3' (SEQ ID No 16) and 5'ACGCAATGGTGAGTTGTAC-3' (SEQ ID No 17).

C. DNA Sequence Analysis:

The PCR products were cloned into either pUC119 or pGEM-Teasy (Promega Corp.). The nucleotide sequence of inserts was obtained by the chain termination method using the fmol sequencing system (Promega Corp.).

Example 2

Tests Showing that Hahb-4 is Induced by Lack of Water

A. Plant Material, Growth Conditions and Water Stress Treatments

*Helianthus annuus* L. (sunflower cv. contiflor 15, from Zeneca, Balcarce, Argentina, or cv. Sunweed, from Rhône-Poulenc, Lyon, France) seeds were surface sterilized and grown on filter paper inside Petri dishes for a period of 4 d. Seedlings were then transferred to plastic supports containing Hoagland's medium and grown until they had six leaves (approximately 3 weeks). Water stress was imposed either by transferring 4-day-old-seedlings to Petri dishes with dry filter paper or by removing plants from the hydroponic culture. The treatment times were as indicated in the figures.

B. RNAse Protection Analysis:

For RNAse protection analysis, total RNA (15 µg) prepared as described (Almoguera C., et. al.; Plant molecular Biology 19: 781-792, 1992) was hybridized to a specific Hahb-4 riboprobe synthesized by in vitro transcription using T3 RNA polymerase and [$^{32}$P]CTP following the instructions of the manufacturer (Boehringer Mannheim, Mannheim, Germany). The template consisted of an insert corresponding to the coding region between +81 and +429 (FIG. 1 and SEQ ID No 1) cloned into the SpeI/BamHI sites of pBlue-script SK⁻. The BamHI site, not present in the cDNA, derives from amplification with oligonucleotide H41 as described above. Restriction digestion of this template DNA with EcoRI allows transcription of a 411-nucleotide RNA probe that contains 63 nucleotides from the vector (from the T3 promoter to the SpeI site in the polylinker, and from the BamHI to the EcoRI sites). Conditions for riboprobe preparation, hybridization, digestion with RNAse A, and subsequent electrophoretic analysis of protected RNA fragments were as previously described (Coca M: A: et. al.; Plant Molecular Biology 31: 863-876, 1996, herein incorporated as reference).

C. Northern Analysis:

Total RNA (20 µg) was denatured with formamide and formaldehyde, separated in a 1-5% (w/v) agarose/6% formaldehyde gel, and blotted onto nylon membranes (Hybond N; Amersham-Pharmacia, Buckinghamshire, UK) essentially as described by Sambrook, Fritsch & Maniatis (1989).

Hybridization was performed overnight at 65° C. in 6×SSC (1×SSC is 0.15 M NaCl, 0.015 M Na$_3$-citrate, pH 7.0), 0.1% (w/v) polyvinylpirrolidone, 0.1% (w/v) bovine serum albumin, 0.1% (w/v) Ficoll, 0.5% (w/v) sodium dodecyl sulphate (SDS). An SpeI/EcoRI fragment (from +424 to +674), corresponding to the 3' non coding region of the Hahb-4 cDNA plus the last 177 nucleotides of the coding region, which does not include the Hd-Zip domain, was labeled with [$^{32}$P]dATP ($1\times10^8$ dpm µg$^{-1}$) by random priming (Sambrook et al. 1989) and used as probe. The filters were autoradiographed using Bio-Max films and transcreen (Eastman Kodak, Rochester, N.Y., USA) overnight. To check the amount of total RNA loaded in each lane, filters were then re-probed with a 25S rRNA from Vicia faba under similar conditions as those described above, except that hybridization was performed at 62° C.

D. Preparation of Nuclei:

Sunflower nuclei and nuclear extracts were prepared from control, water-stressed, or ABA-treated seedlings (4-days-old) according to the technique described in Maliga et al. (Methods in Plant Molecular Biology. A Laboratory Course Manual, pages 233-260. Cold Spring Harbor Laboratory Press, Cold Spring Harbor, N.Y., USA, 1995, herein incorporated by reference). Protein patterns were analyzed by SDS-polyacryla-mide gel electrophoresis (PAGE) and total protein concentration was measured as described Sedmak J. et. al., Analytical Biochemistry 79: 544-552, 1977.

E. DNA-Binding Assays:

For electrophoretic mobility shift assays (EMSA), aliquots of purified nuclear proteins (30 µg) were incubated with double-stranded DNA (0.3-0.6 ng, 30 000 c.p.m., labeled with [$^{32}$P]dATP by filling-in the 3'ends using the Klenow fragment of DNA polymerase) generated by either hybridization of the complementary oligonucleotides 5'-AATTCA-GATCTCAATAATTGAGAG-3' and 5'-GATCCTCTCAAT-TATTGAGATCTG-3' (SEQ ID No 18 and SEQ ID No 19) (binding site for Hahb-4 is underlined). Binding reactions (20 µL) containing 20 mM HEPES-NaOH (pH 7.6), 40 mM NaCl, 0-2 mM ethylenedi-aminetetraacetic acid (EDTA), 1.0 mM dithiothreitol (DTT), 0.5% Triton X-100, 20% glycerol, and 1.5 µg poly(dI-dC), were incubated for 20 min at 25° C., supplemented with 2.5% (w/v) Ficoll and immediately loaded onto a running gel (5% acrylamide, 0.08% bis-acrylamide in 0.5×TBE plus 2.5% glycerol; 1×TBE is 90 mM Tris-borate, pH 8.3, 2 mM EDTA). The gel was run in 0.5× TBE at 30 mA for 1.5 h and dried prior to autoradiography.

Example 3

Test for Providing Tolerance to the Water Stress in *Arabidopsis thaliana* Employing the Sunflower Hahb-4 of the Invention A. Biologic Material:

*E. coli* DH5α strain and *Agrobacterium tumefaciens* GV2260 strain were employed. For the transforming plants tests seeds of *Arabidopsis thaliana* ecotype Columbia-0 were used.

B. Molecular Cloning:

For cloning Hahb-4 under the control of CaMV35S promoter a PCR reaction was carried out by using [as template] the clone corresponding to cDNA (Gago et al., Plant Cell & Environment 25: 633-640, 2002, herein incorporated as a reference) and two specific oligonucleotides T1: 5'-GCGG-GATCCACCATGTCTCTTCAACAAGTA-3'; (SEQ ID No 20) and T2: 5'-GCCGAGCTCTTAGAACTCCCAACCAC-CTTTTG-31 (SEQ ID No 21) that hybridized in both ends of the coding region. In this manner regions 3' and 5' that do not encode the messenger ARN are eliminated thus decreasing the possible effects of post-transcriptional regulation. These oligonucleotides were designed in a manner that they can introduced in the amplified fragment in sites BamHI and SacI of the plasmid. In addition, the sequence established as consensus for an optimal translation was added to the oligonucleotide in the 5'cDNA end (oligonucleotide T1). The product of the PCR reaction was purified and digested with the above mentioned enzymes and cloned into pBI 121 vector using *E. coli* for the transformation. Once the desired clone was obtained the plasmidic DNA was introduced in *A. tumefaciens* according to the method disclosed by Höfgen and Willmitzer (Höfgen and Willmitzer, Nucleic Acid Research 16: 9977, 1998). The *Agrobacterium* strain having the pBI 121 plasmid where the gus gene has been replaced by Hahb-4 was called ATH4.

The cloning and checking techniques were taken from Sambrook, J., Fritsch, E. F. and Maniatis, T. (1989) *Molecular Cloning: A Laboratory Manual*. Second edition. Cold Spring Harbor Laboratory Press, Cold Spring Harbor, N.Y.

C. *Arabidopsis thaliana* Transformation:

The method employed for transforming *Arabidopsis thaliana* was the one using immersion (floral dip) described by Clough and Bent (Clough and Bent, Plant J. 16: 735-743, 1998). The seeds recovered from the transforming test were sterilized and cultured in Petri dishes containing medium MS supplemented with kanamycin 40 mg/l. The resistant plants (F1) were passed into soil and maintained up to produce seeds. The resulting lines (F2) were analyzed for the presence of the transgene (Hahb-4 gene) using PCR and the expression of the corresponding transcript was also analyzed by Northern. The lines expressing the transgene were reproduced up to obtain homozygote sub-lines.

The preparations of total RNA from *Arabidopsis thaliana* were carried out according to the method disclosed by Carpenter and Simon (Carpenter, C. and Simon, A. (1998) Preparation of RNA. EnIn: *Methods in Molecular Biology*, vol 82: *Arabidopsis Protocols*. J. M. Martinez-Zapater and J. Salinas (Eds.), Humana Press Inc., Totowa, N.J.). For the Northern analysis, disclosed processes have been carried out (Ausubel, F. M., Brent, R., Kingston, R. E., Moore, D. D., Seidman, J. G., Smith, J. A. and Struhl, K. (1983) *Current Protocols in Molecular Biology*. John Wiley & Sons, N.Y.

For analyzing the *Arabidopsis thaliana* transformed plants by PCR technique preparations of total DNA were made by employing a rapid method disclosed by Li and Chory (Li, J. and Chory, J. (1998) Preparation of DNA from *Arabidopsis*. In: *Methods in Molecular Biology*, vol. 82: *Arabidopsis Protocols*. J. M. Martinez-Zapater and J. Salinas (Eds.), Humana Press Inc., Totowa, N.J.)

D. Phenotypic Analysis:

D1. Analysis in Petri Plates:

The seeds from *Arabidopsis thaliana* were sterilized by washing with ethanol 70% (v/v) (1 min), chlorine 5%-SDS 1% (15 min) and sterile distilled water (3 times). Then the seeds were suspended in 8 ml of agar 0.1% and sowed in 150 mm Petri plates containing MS medium, with the addition of Gamborg's vitamins. The plates were maintained at 4° C. during two days and then placed into a culture chamber with controlled light and temperature (16 hours light at 24° C. and 8 hours darkness at 21° C.). The required illumination conditions (150-200 $\mu$E/m 2) were artificially obtained by keeping the plants at a distance of 25 cm from six fluorescent tubes, intercalating white light and Grolux tubes (from Sylvania) adjacently located.

The handling of plant material was done in sterile conditions. The MS culture medium was sterilized in autoclave and subsequently vitamins were added by filtration.

D2: Tests in Soil:

The tests in soil were carried out in 12 cm diameter and 10 cm high pots. Depending on the test, each pot was sowed with about one to three seeds from *Arabidopsis* equidistantly distributed. The tray was covered with transparent plastic material until the appearance of the seedling, then the plastic was removed. Each 16 pots were placed in a plastic tray and the growing of the plants was followed in a culture chamber under the same above disclosed illumination conditions. Irrigation water was supplemented in the plastic trays.

For carrying out water stress tests the tray was supplemented from the beginning with 1, 1.5 or 2 litres of water. In all the cases no additional water was added until the end of the reproductive cycle. These irrigation conditions, by keeping the culture chamber under very low humidity conditions, generates in the plants a water stress when they have two pairs of leaves, complete rosette or developed flowers respectively. Water stress can be visualized from the dryness and cracking of the soil, the loss of turgence in the leaves and finally the death of the plants.

Example 4

Isolation and Characterization of Hahb-4 Promoter, Constructs Containing Different Fragments of the Promoter and Transgenic Plants from *A. Thaliana* Containing said Constructs A. Vegetal Material, Culturing and Treating Conditions:

Sunflower seeds from Contiflor 15 culture (*Helianthus annuus* L.) (Zeneca) have been employed. For the plant transformation tests seeds from *Arabidopsis thaliana* ecotype Columbia-0 were used.

The seeds from *Arabidopsis thaliana* were sterilized by washing in ethanol 70% (v/v) (1 min), chlorine 5%-SDS 1% (15 min) and sterile distilled water (3 times). Subsequently the seeds were re-suspended in agar 8 ml at 0.1% and sowed in 150 mm Petri plates containing MS medium, with the addition of Gamborg's vitamins. The plates were maintained at 4° C. for two days and then were placed into a culture chamber with controlled light and temperature (16 hours light at 24° C. and 8 hours darkness at 21° C.).

Culturing of plants from *Arabidopsis thaliana* was carried out in a chamber with controlled light and temperature (16 hours with light at 24° C. and 8 hours in darkness at 21° C.). The required illumination conditions (150-200 $\mu$E/m 2) were artificially obtained by keeping the plants at a distance of 60 cm from six fluorescent tubes, intercalating white light tubes and Grolux tubes (from Sylvania) adjacently located.

B. Purification of Plant DNA:

For extracting total DNA from plants the method disclosed by Doyle y Doyle (Doyle, J. J. and Doyle, J. L. (1987) was used. A rapid DNA isolation procedure for small quantities from fresh leaf tissue. *Phytochemical Bulletin* 19, 11-15) has been carried out.

C. Plasmids, Strains and Molecular Cloning Methods Employed:

The pGEM.-T easy plasmid (Promega), was used for cloning products from amplification reactions with Taq DNA polymerase (Promega).

pBI101 plasmid (Jefferson et al., EMBO J. 6: 3901-3907, 1987) was also used, the plasmid being a derivative of pBIN19 binary vector. It contains the gene encoding *E. coli* $\beta$-glucuronidase (gus) with the polyadenilation signal from nopaline synthetase (nos). It also contains nptII gene conferring resistance to kanamycin in plants. Other sequences that are relevant in the vector include the gene providing resistance to kanamycin in bacteria and a bacteria replication origin RK2. This plasmid was used for cloning different fragments of sunflower Hahb-4 promoter in *Arabidopsis thaliana*, in unique restriction sites located upstream of gus gene.

Cloning constructs in T-easy or pBI vector was firstly made by using competent host cells of *E. coli* DH5$\alpha$ following classic transformation protocols or electroporation as described in Sambrook (Sambrook, J., Fritsch, E. F. and Maniatis, T. (1989) *Molecular Cloning: A Laboratory Manual*. Second edition. Cold Spring Harbor Laboratory Press, Cold Spring Harbor, N.Y.). For preparing competent cells of *A. tumefaciens* and further transformation thereof the method described by Höfgen and Willmitzer has been followed (Höfgen, R. and Willmitzer, L. (1988) Storage of competent *Agrobacterium* cells for transformation was carried out according to. *Nucleic Acids Res.* 16, 1977).

D. Molecular Cloning of DNA Fragments:

For cloning the promoting region of the inventive gene the strategy of inverse PCR described by Ochman et al. has been employed (Ochman, H., Ayala, F. J. and Hartl, D. L. (1993) Use of polymerase chain reaction to amplify segments outside boundaries of known sequences. In: *Methods in Enzimology* vol 218. R. Wu (Ed.), Academic Press, San Diego, Calif.), was carried out as follows.

The extraction of sunflower genomic DNA was made as described above, providing 5 $\mu$g of DNA and 1-3 U of SauIIIA or HindIII (Promega) per microgram of DNA were used. Once the digestion was verified (by sowing an aliquot in agarose gel 0.7% (p/v)), the fragments were precipitated by the addition of $\frac{1}{10}$ vol. of 3 M NaAc (pH 5.2) and 2 volumes of absolute ethanol.

For enhancing the re-ligation of the restriction fragments, the reactions were carried out in a final volume 100 $\mu$l. 2, 10 and 20 ng of the fragments obtained in each reaction and 5U T4 DNA ligase (Promega) were employed. The reactions were carried out for 16 hours at 14° C. The fragments were precipitated and purified for use as template in a PCR reaction.

Figure 23:
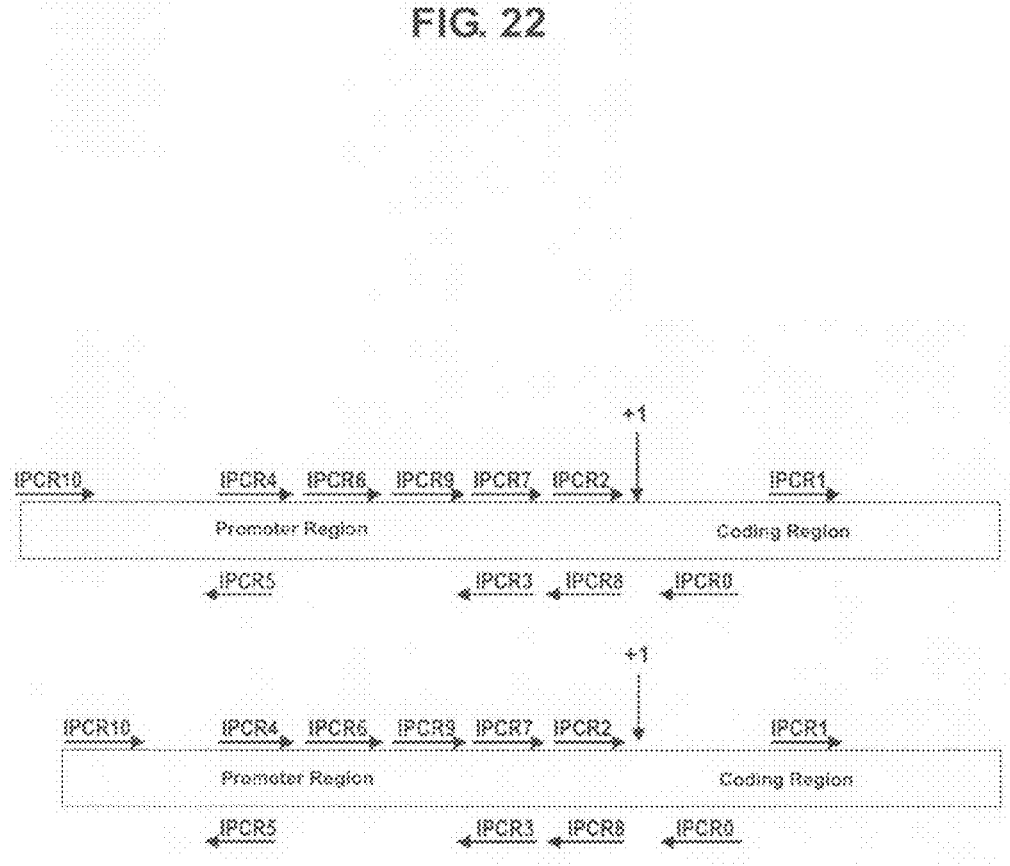
FIG. 23 shows a scheme of Hahb-4 gene structure. At the top: large allele, at the bottom: small allele. The oligonucleotides employed for the isolation of the promoting region and for the construction of recombinant plasmids and used in plant transformation are indicated.

The PCR reactions in the first step were made by using as a template the DNA from the recycling of the fragments digested with SauIIIA, with oligonucleotides IIPCR0/IPCR1 (SEQ ID NO:12/SEQ ID NO:15) and in the case of the DNA digested with HindIII, the employed oligonucleotides were IPCR2/IPCR3 (SEQ ID NO:16/SEQ ID NO:17). The obtained fragments were cloned in pGEM®-T easy vector (Promega), according to the protocol suggested by the manufacturer. Once the cloning was verified, the corresponding sequence was determined and the oligonucleotides necessary for the next step were designed. The sequence and location of the oligonucleotides used in the next cloning steps are shown in FIG. 23:

```
IPCR0   [5'-GGCGGATCCCCTGGTGGTTGTTTCTGTTG-3']      (SEQ ID NO:12)

IPCR1   [5'-GCCGAATTCAGATTGAGCAAGAGTATAAC-3']      (SEQ ID NO:15)

IPCR2   [5'-ACCTTTATAAAGACCACTC-3']                (SEQ ID NO:16)

IPCR3   [5'-ACGCAATGGTGAGTTGTAC-3']                (SEQ ID NO:17)

IPCR4   [5'-GCGAAGCTTGATGCGAACGAGTGGTTTA]          (SEQ ID NO:4)

IPCR5   [5'-ATTTCGCAAGTAGTCCATT-3']                (SEQ ID NO:9)

IPCR6   [5'-CCCAAGCTTAACCTAAGTCCGCCTTTG-3']        (SEQ ID NO:7)

IPCR7   [5'-GGCAAGCTTATCTCAACCGAAAGTGAC-3]         (SEQ ID NO:8)
```

Finally, since this technique is apt for segmented cloning, the knowledge of the sequence for amplifying the complete segment using sunflower genomic DNA as mold[template], the polymerase chain reaction, and two oligonucleotides designed in such a manner to hybridize the opposite ends (IPCR10: GCGGTCGACACCTGGCACATCGTATCT (SEQ ID No 5) and IPCR8: CGCGGATC-CGAGGGTTTGATAAGTGAT (SEQ ID No 6)) were used. The amplification product was cloned in PGEM-Teasy vector and subsequently its sequence was determined.

The strategy used for the inverse PCR as well as for the construction of recombinant plasmids used in the transformation of plants are shown in FIG. 23.

The different fragments of the promoter including the transcription initiation site were afterwards cloned into pBI101.3 vector. Alternatively, for studying the promoter segments that are distant from the transcription initiation site, a modified pBI vector carrying a minimum promoter (−90 CaMV35S) including TATA box was employed. This vector also contains the gus gene as a reporter thus permitting to measure the promoting activity of each cloned segment.

E. Cloning of Hahb-4 Intron:

For cloning the hahb-4 intron a PCR reaction was carried out by using as template sunflower genomic DNA and the oligonucleotides IPCR1 (5%-GCCGAATTCAGATTGAG-CAAGAGTATAAC-3 (SEQ ID No 15) y N1 (5'-GCGG-GATCCGTCTGGCAGTTGTTCTTC-3'SEQ ID No 22)). The obtained product was digested with EcoRI and BamHI (sites provided by the nucleotides) and subsequently cloned into pUC119 plasmid previously digested with the same enzymes. Once verifying the presence of the insert having the expected size in some of the white obtained colonies, its sequence was determined as described below.

F. Transformation of Plants from *Arabidopsis thaliana* with the Constructs Obtained in the Prior Stage.

The method employed for transforming plants from *Arabidopsis thaliana* was the immersion method (floral dip) described by Clough and Bent (Clough, S. J. and Bent, A. F. (1998) Floral dip: a simplified method for *Agrobacterium*-mediated transformation of *Arabidopsis thaliana*. Plant J. 16, 735-743).

For each construction, 10-12 pots having a diameter of 10 cm were prepared with soil and covered with a fibber fabric. The cloth was fixed in a manner to be well adhered to the soil surface. Then, the seeds were well spread in the soil and the pots were placed in a tray covered with transparent nylon paper. The plants were cultivated under the above mentioned conditions; after a week the nylon paper was removed and the strongest plants were selected.

The plants were cultured up to the flowering stage (about 4 weeks). When the flower pedicels were breaking out (1-2 cm of the rosette), the inflorescences were cut by taking care of not damaging the caulinar leaves. 4-6 days after the above mentioned cut new inflorescences broke out. It was waited until all the inflorescences had at least not-yet open 4 flowers and then the transformation was carried out.

For preparing the transformation, *A. tumefaciens* suspension cells were cultured in 3 flasks containing 10 ml LB medium supplemented with rifampicin 50 mg/l and kanamycin 50 mg/l for 24 hours at 28° C. with agitation. These cultures were used for inoculating 3 Erlenmeyers containing 200 ml of the same medium and they were grown up to the stationary stage (12-16 hours at 28° C., with agitation). The cells were harvested by centrifugation at 5500×g for 20 minutes. The pellets were resuspended in a liter of 5% sucrose solution containing 300 μl Silwet L-77 (OSI Specialties, Inc.) and the suspension was placed in a precipitating glass with a magnetic stirrer. The plants were submerged for 10 to 60 seconds, trying to prevent the liquid to enter in contact with the soil. Then the pots were placed in a horizontal position in a tray, they were covered by a nylon paper and brought to the culture chamber. Next day the pots were placed in a normal position, water was added into the tray and the plants were left to grow up to the seeds were mature (4-5 weeks).

Finally, the seeds were collected from each pot separately, and the siliques and soil were cleaned manually. Seeds were kept into a refrigerator for further analysis.

For selecting the transformed plants, the seeds collected in the transformation tests were sterilized and sowed in Petri plates containing MS medium supplemented with 40 mg/l kanamycin as it is above disclosed. During the first days in the culture chamber most of the seeds germinated (95%-99%).

At about 10 days the cotyledons of the sensitive plants became yellow while the ones of the transformed plants remained green. The plates were maintained in the chamber for 7 additional days and during this period very green and real leaves were visible only in the transformed plants. The non transformed plants died. The resistant plants were transferred into flowerpots with soil. To prevent humidity suddenly decrease the pots were placed in a tray with water and covered with transparent nylon paper for a week. After this period of time the paper was removed to uncovered the tray and the plants were cultured up to the maturing of the seeds, the seeds were collected and placed into a refrigerator for further analysis. In addition to selecting the plants by their resistance to kanamycin the presence of the transgene was verified by specific PCR.

Finally the homozygote lines of the third plant generation were selected by sowing in plates with kanamycin and observing 100% tolerance in several sublines.

G. Histochemical Analysis of β-Glucuronidase Activity in the Inventive Transformed Plants.

The inventive plants from *A. thaliana* that resulted resistant to kanamycin in the selection and PCR reaction of were subjected to histochemical β-glucuronidase activity test. The tested embryos and organs were washed with buffer 50 mM $Na_2HPO_4$ pH 7. They were then transferred to a solution 50 mM $Na_2HPO_4$ pH 7, 0.1% Tritón X-100, 2 mM X-gluc (5-bromine-4-chlorine-3-indolil β-D-glucuronide), subjected to vacuum for 5 minutes and incubated at 37° C. in darkness between 2 and 12 hours. After incubation they were fixed in 10% formaldehyde solution, 50% ethanol and 5% ascetic acid for 10 minutes at room temperature. Formaldehyde was removed, ethanol 70% was added and conserved at 4° C.

The histochemical analysis was made in 2, 10 and 20 day-old seedlings grown in Petri dishes containing MS medium and 0.8% agar and adult plants grown in flowerpots containing soil.

H. Fluorometric Analysis of β-Glucuronidase Activity in the Inventive Transformed Plants:

The transformed plants that resulted resistant to the antibiotic, confirmed as positive lines by PCR reaction, and that expressed histochemically the enzyme β-glucuronidase were used for studying the regulation of the promoting region by fluorometric tests. Between 30 and 50 seeds of each line were cultured in 30 mm Petri dishes with MS-agar medium. After an appropriate growth, the plants were transferred to tubes with MS liquid medium supplemented or not with ABA and incubated for different times as detailed below. After incubation the plants were maintained in liquid $N_2$ up to their processing.

The protein extract was obtained by homogenization of vegetal material (about 2-5 mg) up to obtain a fine powder. Then 500 µl extraction buffer (50 mM $Na_2HPO_4$ pH 7, 10 mM EDTA, 0.1% SDS, 10 mM β-mercaptoethanol, 1% Tritón X-100) was added. The suspension was transferred into an Eppendorf tube and centrifuged at 13000×g for 10 minutes at 4° C. The supernatant was removed and the pellet was kept in ice.

The fluorometric reaction was made according to the Jefferson method (Jefferson, R. A., Kavanagh, T. A. and Bevan, M. W. (1987) Gus fusions: β-glucuronidase as a sensitive and versatile gene fusion marker in higher plants. *EMBO J.* 6, 3901-3907). 100 µl protein extract were added to 100 µl methanol and 300 A1 substrate MUG (4-methyl umbeliferil β-D-glucuronide). A 100 µl aliquot was extracted and a flurometric measure was immediately made a[t] time 0. The remaining 400 µl were incubated at 37° C. in boiling water and 100 µl aliquots were removed at the times of 30, 60 and 120 minutes. For stopping the reaction 0.9 ml of 0.2 M $Na_2CO_3$ were used. The values of the fluorometric reactions were expressed in pmols of product/mg of total proteins per minute according to a pattern curve of RFU as a function of concentration of product 4-MU (7-hydroxi-4 methyl umbeliferone).

The fluorometric measures were made in an equipment VersaFluor™ Fluorometer System, from Bio-Rad (filters EM 460/10 y EX 360/40) in 1 ml dishes.

I. Quantification of Total Proteins:

The concentration of the soluble proteins of the protein extracts was determined by using the method disclosed by Sedmak y Grossberg (Sedmak, J. and Grossberg, S. (1977) A rapid, sensitive, and versatile assay for protein using Coomassie brilliant blue G-250. *Anal. Biochem.* 79, 544-552). Bovine serum albumin (BSA) was used as pattern.

J. Determination and Analysis of Sequences:

For determining the DNA sequence of the obtained constructs a commercial equipment T7 Sequencing kit (Amersham Biosciences) was used, the method being based on the Sanger method (Sanger, F., Nicklen, S. and Coulson, A. R. (1977) DNA sequencing with chain-terminating inhibitors. *Proc. Natl. Acad. Sci. USA* 74, 5463-5467), combining DNA extension/termination in only one step. Furthermore, these sequences were confirmed in an automatic sequencer (Service given High Complexity Laboratory, INTA, Castelar, Bs. As. Argentina).

For identifying the regulating sequences within the promoting regions the data bases PLACE (Higo, K., Ugawa, Y., Iwamoto, M. and Korenaga, T. (1999) Plant cis-acting regulatory DNA elements (PLACE) database: 1999. *Nucleic Acids Res.* 27, 297-300) and PlantCARE (Rombauts, S., Dehais, P., Van Montagu, M. and Rouze, P. (1999) Plant-CARE, a plant cis-acting regulatory element database. *Nucleic Acids Res.* 27, 295-296) were used.

When the employed technique is not specified the classical protocols disclosed in Sambrook, J., Fritsch, E. F. and Maniatis, T. (1989) *Molecular Cloning: A Laboratory Manual*. Second edition. Cold Spring Harbor Laboratory Press, Cold Spring Harbor, N.Y. and Ausubel, F. M., Brent, R., Kingston, R. E., Moore, D. D., Seidman, J. G., Smith, J. A. and Struhl, K. (1983) *Current Protocols in Molecular Biology*. John Wiley & Sons, N.Y., have been employed While preferred embodiments of the present invention have been illustrated and described, it will be obvious to those skilled in the art that various changes and modifications may be made therein without departing from the scope of the invention as defined in the appended claims.

We claim:

1. A transgenic plant stably transformed with a nucleic acid molecule comprising an isolated nucleic acid sequence that encodes a protein comprising (1) a Hd-Zip domain that binds SEQ ID NO:23 attached to (2) SEQ ID NO:30, wherein the nucleic acid molecule is expressed in the plant and the expression of the nucleic acid provides an increased tolerance to drought as compared to a wild type variety of such plant under the same conditions.

2. The transgenic plant of claim 1, wherein the plant is a monocot.

3. The transgenic plant of claim 1, wherein the plant is a dicot.

4. A plant seed stably transformed with a nucleic acid molecule comprising an isolated nucleic acid sequence that encodes a protein comprising (1) a Hd-Zip domain that binds SEQ ID NO:23 attached to (2) SEQ ID NO:30, wherein the nucleic acid molecule is expressed in the seed and the expression of the nucleic acid provides an increased tolerance to drought as compared to a wild type variety of such plant seed under the same conditions.

5. A plant host cell that has been stably transformed with a nucleic acid molecule comprising an isolated nucleic acid sequence that encodes a protein comprising (1) a Hd-Zip domain that binds SEQ ID NO:23 attached to (2) SEQ ID NO:30, wherein the nucleic acid molecule is expressed in the plant host cell.

6. A method of producing a water stress tolerant transgenic plant, the method comprising:
stably transforming a plant cell or cell culture with a nucleic acid molecule comprising an isolated nucleic acid sequence that encodes a protein comprising (1) a Hd-Zip domain that binds SEQ ID NO:23 attached to (2) SEQ ID NO:30, wherein the nucleic acid is expressed in the plant cell or cell culture; and regenerating the cell or cell culture into a plant.

7. The transgenic plant of claim 1, wherein said nucleic acid sequence encodes SEQ ID NO:24.

8. The transgenic plant of claim 1, wherein said nucleic acid sequence is selected from the group consisting of SEQ ID NO:1 and SEQ ID NO:2.

9. The plant seed of claim 4, wherein said nucleic acid sequence encodes SEQ ID NO:24.

10. The plant seed of claim 4, wherein said nucleic acid sequence is selected from the group consisting of SEQ ID NO:1 and SEQ ID NO:2.

11. The plant host cell of claim 5, wherein said nucleic acid sequence encodes SEQ ID NO:24.

12. The plant host cell of claim 5, wherein said nucleic acid sequence is selected from the group consisting of SEQ ID NO:1 and SEQ ID NO:2.

13. The method of claim 6, wherein said nucleic acid sequence encodes SEQ ID NO:24.

14. The method of claim 6, wherein said nucleic acid sequence is selected from the group consisting of SEQ ID NO:1 and SEQ ID NO:2.

* * * * *

SEQUENCE LISTING

<160> NUMBER OF SEQ ID NOS: 30

<210> SEQ ID NO 1
<211> LENGTH: 774

```
<212> TYPE: DNA
<213> ORGANISM: Helianthus annuus

<400> SEQUENCE: 1
tcactagtac cataatattc acaaacacac acacctcaga aacgaagctt gcacataatg      60
tctcttcaac aagtacccac aacagaaaca accaccagga agaaccgaaa cgagggggcgg    120 aaacgattta ccgacaaaca aataagtttc ctagagtaca tgtttgagac acagtcgaga    180
cccgagttaa ggatgaaaca ccagttggca cataaactcg ggcttcatcc tcgtcaagtg    240
gcgatatggt tccagaacaa acgcgcgcga tcaaagtcga ggcagattga gcaagagtat    300
aacgcgctaa agcataacta cgagacgctt gcgtctaaat ccgagtctct aaagaaagag    360
aatcaggccc tactcaatca ggtatggttg caaacttaca atgttgcatt caactattta    420
agtagttttg aattttttgtg acaataaaga ttgacaaatg ttgtttgata attgattaac    480
agttggaggt gctgagaaat gtagcagaaa agcatcaaga gaaaactagt agtagtggca    540
gcggtgaaga atcggatgat cggtttacga actctccgga cgttatgttt ggtcaagaaa    600
tgaatgttcc gttttgcgac ggttttgcgt actttgaaga aggaaacagt ttgttggaga    660
ttgaagaaca actgccagac cctcaaaagt ggtgggagtt ctaaagagta aagaaggatg    720
tagaagtagt agagtaaaaa ctaaaacata ccagatagtt ggtttacact ttgt          774

<210> SEQ ID NO 2
<211> LENGTH: 673
<212> TYPE: DNA
<213> ORGANISM: Helianthus annuus

<400> SEQUENCE: 2
tcactagtac cataatattc acaaacacac acacctcaga aacgaagctt gcacataatg      60
tctcttcaac aagtacccac aacagaaaca accaccagga agaaccgaaa cgagggggcgg    120 aaacgattta ccgacaaaca aataagtttc ctagagtaca tgtttgagac acagtcgaga    180
cccgagttaa ggatgaaaca ccagttggca cataaactcg ggcttcatcc tcgtcaagtg    240
gcgatatggt tccagaacaa acgcgcgcga tcaaagtcga ggcagattga gcaagagtat    300
aacgcgctaa agcataacta cgagacgctt gcgtctaaat ccgagtctct aaagaaagag    360
aatcaggccc tactcaatca gttggaggtg ctgagaaatg tagcagaaaa gcatcaagag    420
aaaactagta gtagtggcag cggtgaagaa tcggatgatc ggtttacgaa ctctccggac    480
gttatgtttg gtcaagaaat gaatgttccg ttttgcgacg gttttgcgta ctttgaagaa    540
ggaaacagtt tgttggagat tgaagaacaa ctgccagacc ctcaaaagtg gtgggagttc    600
taaagagtaa agaaggatgt agaagtagta gagtaaaaac taaaacatac cagatagttg    660
gtttacactt tgt                                                      673

<210> SEQ ID NO 3
<211> LENGTH: 1221
<212> TYPE: DNA
<213> ORGANISM: Helianthus annuus
<220> FEATURE:
<221> NAME/KEY: promoter
<222> LOCATION: (1)..(1221)
<223> OTHER INFORMATION: Large allele

<400> SEQUENCE: 3
gatccaattg gaccacctgg cacatcgtat cttatctctt ttgtcgtttc caacacacca      60
caacacacct acaaacgtgt caattcacac ttcaccaatt tcatttcctt ttagtcaatc    120
atattaaaag tagtagcccc caccccccatt tgttacctac catttcccac tttaataatc    180
```

```
acccacgcta tgtccacttg tactttgtt tgcacacaac tcttcccata aaatatcaaa      240
ccaaattttt tttagtggaa acaaattcc ccaaatagaa tactaacgaa attcatcgca      300
tcagaataca ctcatctctg aacagtggcg aagcttgacg ttttcgacgg ggggtcggaa      360
aacgtatgta cccgaaattt ctatagaatc gggggggtcga aaacgtatat acccaaaatt   420
tctatacgaa aactacatat ataacactac tgagcaaaaa gttcgggggt tcgggcgccc    480
ctcccggccc cttcaaagct tcgccaatgt ctctgaaccg aagaaaaccc tcactcgtct    540
actagccaat gaatcctcac cagggaaacc ctcactcgtc ttactggact attggcgctt    600
ccaaatggac tacttgcgaa attcaccaca tcgggataca ctcgtctact gcggtgaggt    660
aaaacccgct tggctcaagg atcgaactag cgattgctgc ctactcgcct aatctcccat    720
catcaacagg tgccgccgaa acaaaatgct ggggcggga gttgaaccta ggtccagtga     780
cgcacccatg aattttttt ctagggatgc gaacgagtgg tttaaccata cttttaagag      840
gtgcgatcgg aaattttacc tataaaatac actaaaaaag ttccaagggt ccacccaccc    900
cttaacctaa gtccgccttt gtctggatca cgtgaaacat caggtctctc ccttaccagt    960
ccagctacga ctcattgaca aaatatcaaa accatatgat tttgagtttt atctcaaccg    1020
aaagtgacat catgacagag aatcgacata accaaaacgt gtaaacgtac aactcaccat    1080
tgcgttgaaa aggacaaaac aggtaggatt cttgtcaaat tcaacgcgta cacctgtgct    1140
tcatctaaac cccatacttt aagaaccttt ataagacca ctcactatat atacacatat     1200
ataatatcac ttatcaaacc c                                               1221

<210> SEQ ID NO 4
<211> LENGTH: 28
<212> TYPE: DNA
<213> ORGANISM: Artificial Sequence
<220> FEATURE:
<223> OTHER INFORMATION: Designed oligonucleotide having a Hind III site

<400> SEQUENCE: 4
gcgaagcttg atgcgaacga gtggttta                                         28

<210> SEQ ID NO 5
<211> LENGTH: 28
<212> TYPE: DNA
<213> ORGANISM: Artificial Sequence
<220> FEATURE:
<223> OTHER INFORMATION: Designed oligonucleotide having a Sal I site

<400> SEQUENCE: 5
gcggtcgaca cctggcacat cgtatctt                                         28

<210> SEQ ID NO 6
<211> LENGTH: 27
<212> TYPE: DNA
<213> ORGANISM: Artificial Sequence
<220> FEATURE:
<223> OTHER INFORMATION: Designed oligonucleotide having a Bam HI site

<400> SEQUENCE: 6
cgcggatccg agggtttgat aagtgat                                          27

<210> SEQ ID NO 7
<211> LENGTH: 27
<212> TYPE: DNA
<213> ORGANISM: Artificial Sequence
<220> FEATURE:
<223> OTHER INFORMATION: Designed oligonucleotide having a Hind III site
```

<400> SEQUENCE: 7
cccaagctta acctaagtcc gcctttg         27

<210> SEQ ID NO 8
<211> LENGTH: 27
<212> TYPE: DNA
<213> ORGANISM: Artificial Sequence
<220> FEATURE:
<223> OTHER INFORMATION: Designed oligonucleotide having a Hind III site

<400> SEQUENCE: 8
ggcaagctta tctcaaccga aagtgac         27

<210> SEQ ID NO 9
<211> LENGTH: 19
<212> TYPE: DNA
<213> ORGANISM: Artificial Sequence
<220> FEATURE:
<223> OTHER INFORMATION: Designed oligonucleotide based on the 5'
      promoter

<400> SEQUENCE: 9
atttcgcaag tagtccatt         19

<210> SEQ ID NO 10
<211> LENGTH: 1015
<212> TYPE: DNA
<213> ORGANISM: Helianthus annuus

<400> SEQUENCE: 10
gatccaattg gaccacctgg cacatcgtat cttatctctt ttgtcgtttc caacacacca     60
caacacacct acaaacgtgt caattcacac ttcaccaatt tcatttcctt ttagtcaatc    120
atattaaaag tagtagcccc caccccccatt tgttacctac catttcccac tttaataatc    180
acccacgcta tgtccacttg tacttttgtt tgcacacaac tcttcccata aaatatcaaa    240
ccaaattttt tttaatggaa acaaatact tcaaatgcac tattggtgaa attcaccaca    300
tcagaataca cccgtctcta ctcatctact ggccaacgaa tcttcacggg ggaaaccctc    360
actcgtctac tgggactact ggcgcttcaa aatggactac tgacaaaatt caccacatcg    420
ggatacactt gtctactgcg gtgaggtaaa atccgccgct cagctcaatg atcgaactag    480
cgatcgccac ccactcacct tgtctcccat catcaccagg tgccgccaaa acaaaatgtt    540
gggggcggga attgaaccta ggtccagtgg cgcacccatg aatttttttt ctagggatgc    600
gaacgagtga tttaaccata cttttaagag gtgcgatcgg aaattttacc tataaaatat    660
actaaaaaaa tttcaagggt ccgcccaccc accccttaac ctaagtccgc ctctgcctgg    720
atcacgtgaa acatcaggtc tctctcttac cagttcacct acaactcatt gacaaaatat    780
caaaaccata tgattttgag ttttatctca accgaaagtg acatcatgac agagaatcga    840
cataaccaaa acgtgtaaac gtacaactca ccattgcgtt gaaaaggaca aaacaggtag    900
gattcttgtc aaattcaacg cgtacacctg tgcttcatct aaacccccata ctttaagaac    960
ctttataaag accactcact atatatacac atatataata tcacttatca aaccc         1015

<210> SEQ ID NO 11
<211> LENGTH: 28
<212> TYPE: DNA
<213> ORGANISM: Artificial Sequence
<220> FEATURE:
<223> OTHER INFORMATION: Designed oligonucleotide having a Bam HI site

```
<400> SEQUENCE: 11
ggcggatcca acagaaacaa ccaccagg                                            28

<210> SEQ ID NO 12
<211> LENGTH: 29
<212> TYPE: DNA
<213> ORGANISM: Artificial Sequence
<220> FEATURE:
<223> OTHER INFORMATION: Designed oligonucleotide having a Bam HI site

<400> SEQUENCE: 12
ggcggatccc ctggtggttg tttctgttg                                           29

<210> SEQ ID NO 13
<211> LENGTH: 34
<212> TYPE: DNA
<213> ORGANISM: Artificial Sequence
<220> FEATURE:
<223> OTHER INFORMATION: Designed oligonucleotide having a Xho I site

<400> SEQUENCE: 13
gaggactcga gctcaagttt tttttttttt tttt                                     34

<210> SEQ ID NO 14
<211> LENGTH: 18
<212> TYPE: DNA
<213> ORGANISM: Artificial Sequence
<220> FEATURE:
<223> OTHER INFORMATION: Designed Oligonucleotide having a Xho I site

<400> SEQUENCE: 14
gaggactcga gctcaagc                                                       18

<210> SEQ ID NO 15
<211> LENGTH: 29
<212> TYPE: DNA
<213> ORGANISM: Artificial Sequence
<220> FEATURE:
<223> OTHER INFORMATION: Designed oligonucleotide having an Eco RI site

<400> SEQUENCE: 15
gccgaattca gattgagcaa gagtataac                                           29

<210> SEQ ID NO 16
<211> LENGTH: 19
<212> TYPE: DNA
<213> ORGANISM: Artificial Sequence
<220> FEATURE:
<223> OTHER INFORMATION: Designed oligonucleotide based on the promoter

<400> SEQUENCE: 16
acctttataa agaccactc                                                      19

<210> SEQ ID NO 17
<211> LENGTH: 19
<212> TYPE: DNA
<213> ORGANISM: Artificial Sequence
<220> FEATURE:
<223> OTHER INFORMATION: Designed oligonucleotide based on the promoter

<400> SEQUENCE: 17
acgcaatggt gagttgtac                                                      19

<210> SEQ ID NO 18
<211> LENGTH: 24
<212> TYPE: DNA
```

-continued

<213> ORGANISM: Artificial Sequence
<220> FEATURE:
<223> OTHER INFORMATION: Designed oligonucleotide to DNA-binding assays

<400> SEQUENCE: 18
aattcagatc tcaataattg agag                                            24

<210> SEQ ID NO 19
<211> LENGTH: 24
<212> TYPE: DNA
<213> ORGANISM: Artificial Sequence
<220> FEATURE:
<223> OTHER INFORMATION: Designed oligonucleotide to DNA-binding assays

<400> SEQUENCE: 19
gatcctctca attattgaga tctg                                            24

<210> SEQ ID NO 20
<211> LENGTH: 30
<212> TYPE: DNA
<213> ORGANISM: Artificial Sequence
<220> FEATURE:
<223> OTHER INFORMATION: Designed Oligonucleotide having a Bam HI site

<400> SEQUENCE: 20
gcgggatcca ccatgtctct tcaacaagta                                      30

<210> SEQ ID NO 21
<211> LENGTH: 30
<212> TYPE: DNA
<213> ORGANISM: Artificial Sequence
<220> FEATURE:
<223> OTHER INFORMATION: Designed Oligonucleotide having a Sac I site

<400> SEQUENCE: 21
gccgagctct tagaactcca accacttttg                                      30

<210> SEQ ID NO 22
<211> LENGTH: 27
<212> TYPE: DNA
<213> ORGANISM: Artificial Sequence
<220> FEATURE:
<223> OTHER INFORMATION: Designed Oligonucleotide having a Bam HI site

<400> SEQUENCE: 22
ggcggatccg tctcccagtt gttcttc                                         27

<210> SEQ ID NO 23
<211> LENGTH: 9
<212> TYPE: DNA
<213> ORGANISM: Helianthus annuus
<220> FEATURE:
<221> NAME/KEY: misc_feature
<222> LOCATION: (5)..(5)
<223> OTHER INFORMATION: n is a or t

<400> SEQUENCE: 23 caatnattg                                                              9

<210> SEQ ID NO 24
<211> LENGTH: 181
<212> TYPE: PRT
<213> ORGANISM: Helianthus annuus

<400> SEQUENCE: 24

Met Ser Leu Gln Gln Val Pro Thr Thr Glu Thr Thr Thr Arg Lys Asn
1               5                   10                  15

Arg Asn Glu Gly Arg Lys Arg Phe Thr Asp Lys Gln Ile Ser Phe Leu
            20                  25                  30

Glu Tyr Met Phe Glu Thr Gln Ser Arg Pro Glu Leu Arg Met Lys His
        35                  40                  45

Gln Leu Ala His Lys Leu Gly Leu His Pro Arg Gln Val Ala Ile Trp
    50                  55                  60

Phe Gln Asn Lys Arg Ala Arg Ser Lys Ser Arg Gln Ile Glu Gln Glu
65                  70                  75                  80

Tyr Asn Ala Leu Lys His Asn Tyr Glu Thr Leu Ala Ser Lys Ser Glu
                85                  90                  95

Ser Leu Lys Lys Glu Asn Gln Ala Leu Leu Asn Gln Leu Glu Val Leu
            100                 105                 110

Arg Asn Val Ala Glu Lys His Gln Glu Lys Thr Ser Ser Ser Gly Ser
        115                 120                 125

Gly Glu Glu Ser Asp Asp Arg Phe Thr Asn Ser Pro Asp Val Met Phe
130                 135                 140

Gly Gln Glu Met Asn Val Pro Phe Cys Asp Gly Phe Ala Tyr Phe Glu
145                 150                 155                 160

Glu Gly Asn Ser Leu Leu Glu Ile Glu Glu Gln Leu Pro Asp Pro Gln
                165                 170                 175

Lys Trp Trp Glu Phe
            180

<210> SEQ ID NO 25
<211> LENGTH: 99
<212> TYPE: PRT
<213> ORGANISM: Artificial Sequence
<220> FEATURE:
<223> OTHER INFORMATION: Synthetic Hd-Zip domain of Athb-1

<400> SEQUENCE: 25

Leu Pro Glu Lys Lys Arg Arg Leu Thr Thr Glu Gln Val His Leu Leu
1               5                   10                  15

Glu Lys Ser Phe Glu Thr Glu Asn Lys Leu Glu Pro Glu Arg Lys Thr
            20                  25                  30

Gln Leu Ala Lys Lys Leu Gly Leu Gln Pro Arg Gln Val Ala Val Trp
        35                  40                  45

Phe Gln Asn Arg Arg Ala Arg Trp Lys Thr Lys Gln Leu Glu Arg Asp
    50                  55                  60

Tyr Asp Leu Leu Lys Ser Thr Tyr Asp Gln Leu Leu Ser Asn Tyr Asp
65                  70                  75                  80

Ser Ile Val Met Asp Asn Asp Lys Leu Arg Ser Glu Val Thr Ser Leu
                85                  90                  95

Thr Glu Lys

<210> SEQ ID NO 26
<211> LENGTH: 99
<212> TYPE: PRT
<213> ORGANISM: Artificial Sequence
<220> FEATURE:
<223> OTHER INFORMATION: Synthetic Hd-Zip domain of Athb-6

<400> SEQUENCE: 26

Leu Ser Glu Lys Lys Arg Arg Leu Ser Ile Asn Gln Val Lys Ala Leu
1               5                   10                  15

Glu Lys Asn Phe Glu Leu Glu Asn Lys Leu Glu Pro Glu Arg Lys Val
            20                  25                  30

-continued

```
Lys Leu Ala Gln Glu Leu Gly Leu Gln Pro Arg Gln Val Ala Val Trp
            35                  40                  45

Phe Gln Asn Arg Arg Ala Arg Trp Lys Thr Lys Gln Leu Glu Lys Asp
        50                  55                  60

Tyr Gly Val Leu Lys Thr Gln Tyr Asp Ser Leu Arg His Asn Phe Asp
 65                  70                  75                  80

Ser Leu Arg Arg Asp Asn Glu Ser Leu Leu Gln Glu Ile Ser Lys Leu
                85                  90                  95

Lys Thr Lys

<210> SEQ ID NO 27
<211> LENGTH: 99
<212> TYPE: PRT
<213> ORGANISM: Artificial Sequence
<220> FEATURE:
<223> OTHER INFORMATION: Synthetic Hd-Zip domain of Athb-7

<400> SEQUENCE: 27

Asn Lys Asn Asn Gln Arg Arg Phe Ser Asp Glu Gln Ile Lys Ser Leu
 1               5                  10                  15

Glu Met Met Phe Glu Ser Glu Thr Arg Leu Glu Pro Arg Lys Lys Val
                20                  25                  30

Gln Leu Ala Arg Glu Leu Gly Leu Gln Pro Arg Gln Val Ala Ile Trp
            35                  40                  45

Phe Gln Asn Lys Arg Ala Arg Trp Lys Ser Lys Gln Leu Glu Thr Glu
        50                  55                  60

Tyr Asn Ile Leu Arg Gln Asn Tyr Asp Asn Leu Ala Ser Gln Phe Glu
 65                  70                  75                  80

Ser Leu Lys Lys Glu Lys Gln Ala Leu Val Ser Glu Leu Gln Arg Leu
                85                  90                  95

Lys Glu Ala

<210> SEQ ID NO 28
<211> LENGTH: 99
<212> TYPE: PRT
<213> ORGANISM: Artificial Sequence
<220> FEATURE:
<223> OTHER INFORMATION: Synthetic Hd-Zip domain of Athb-12

<400> SEQUENCE: 28

Lys Ser Asn Asn Gln Lys Arg Phe Asn Glu Glu Gln Ile Lys Ser Leu
 1               5                  10                  15

Glu Leu Ile Phe Glu Ser Glu Thr Arg Leu Glu Pro Arg Lys Lys Val
                20                  25                  30

Gln Val Ala Arg Glu Leu Gly Leu Gln Pro Arg Gln Met Thr Ile Trp
            35                  40                  45

Phe Gln Asn Lys Arg Ala Arg Trp Lys Thr Lys Gln Leu Glu Lys Glu
        50                  55                  60

Tyr Asn Thr Leu Arg Ala Asn Tyr Asn Asn Leu Ala Ser Gln Phe Glu
 65                  70                  75                  80

Ile Met Lys Lys Glu Lys Gln Ser Leu Val Ser Glu Leu Gln Arg Leu
                85                  90                  95

Asn Glu Glu

<210> SEQ ID NO 29
<211> LENGTH: 99
<212> TYPE: PRT
<213> ORGANISM: Artificial Sequence
<220> FEATURE:
```

<223> OTHER INFORMATION: Synthetic Hd-Zip domain of Hahb-4

<400> SEQUENCE: 29

```
Arg Asn Glu Gly Arg Lys Arg Phe Thr Asp Lys Gln Ile Ser Phe Leu
1               5                   10                  15
Glu Tyr Met Phe Glu Thr Gln Ser Arg Pro Glu Leu Arg Met Lys His
            20                  25                  30
Gln Leu Ala His Lys Leu Gly Leu His Pro Arg Gln Val Ala Ile Trp
        35                  40                  45
Phe Gln Asn Lys Arg Ala Arg Ser Lys Ser Arg Gln Ile Glu Gln Glu
    50                  55                  60
Tyr Asn Ala Leu Lys His Asn Tyr Glu Thr Leu Ala Ser Lys Ser Glu
65                  70                  75                  80
Ser Leu Lys Lys Glu Asn Gln Ala Leu Leu Asn Gln Leu Glu Val Leu
                85                  90                  95
Arg Asn Val
```

<210> SEQ ID NO 30
<211> LENGTH: 66
<212> TYPE: PRT
<213> ORGANISM: Artificial Sequence
<220> FEATURE:
<223> OTHER INFORMATION: Synthetic fragment of Hahb-4

<400> SEQUENCE: 30

```
Ala Glu Lys His Gln Glu Lys Thr Ser Ser Ser Gly Ser Gly Glu Glu
1               5                   10                  15
Ser Asp Asp Arg Phe Thr Asn Ser Pro Asp Val Met Phe Gly Gln Glu
            20                  25                  30
Met Asn Val Pro Phe Cys Asp Gly Phe Ala Tyr Phe Glu Glu Gly Asn
        35                  40                  45
Ser Leu Leu Glu Ile Glu Glu Gln Leu Pro Asp Pro Gln Lys Trp Trp
    50                  55                  60
Glu Phe
65
```